United States Patent [19]

Lavender

[11] Patent Number: 4,980,054

[45] Date of Patent: Dec. 25, 1990

[54] SYSTEM AND METHOD FOR MASS TRANSFER BETWEEN FLUIDS

[76] Inventor: Ardis R. Lavender, 15 Deerfield Rd., Chappaqua, N.Y. 10514

[21] Appl. No.: 139,647

[22] Filed: Dec. 30, 1987

Related U.S. Application Data

[63] Continuation-in-part of Ser. No. 523,007, Aug. 15, 1983, and a continuation-in-part of Ser. No. 809,923, Dec. 16, 1985, Pat. No. 4,898,675.

[51] Int. Cl.[5] .............................................. B01D 61/18
[52] U.S. Cl. ..................................... 210/90; 210/104; 210/195.2; 210/321.84; 210/456
[58] Field of Search ...................... 210/195.2, 335, 90, 210/336, 104, 85, 456, 651, 639, 641, 321.84

[56] References Cited

U.S. PATENT DOCUMENTS

| | | | |
|---|---|---|---|
| D. 289,548 | 4/1987 | Lavender et al. | D24/1.1 |
| 3,516,548 | 6/1970 | Alwall et al. | 210/321 |
| 3,705,100 | 12/1972 | Blatt et al. | 210/23 |
| 3,969,241 | 7/1976 | Skrabak et al. | 210/336 X |
| 4,110,220 | 8/1978 | Lavender | 210/321 R |
| 4,162,982 | 7/1979 | Chesner | 210/486 |
| 4,212,742 | 7/1980 | Solomon et al. | 210/247 |
| 4,318,813 | 3/1982 | Edelman et al. | 210/321.4 |
| 4,324,658 | 4/1982 | Esmond | 210/321.3 |
| 4,375,415 | 3/1983 | Lavender | 210/651 |
| 4,401,566 | 8/1983 | Igari et al. | 210/351 |
| 4,419,237 | 12/1983 | Esmond | 210/541 X |
| 4,565,073 | 1/1986 | Lavender | 62/373 |
| 4,568,255 | 2/1986 | Lavender et al. | 417/477 |
| 4,592,582 | 6/1986 | Lavender et al. | 294/137 |
| 4,597,868 | 7/1986 | Watanabe | 210/232 |
| 4,610,781 | 9/1986 | Bilstad et al. | 210/85 |

FOREIGN PATENT DOCUMENTS

| | | | |
|---|---|---|---|
| 0021301 | 6/1980 | European Pat. Off. | 210/651 |
| 0045073 | 2/1982 | European Pat. Off. | 210/486 |
| 2112293 | 7/1983 | United Kingdom | 210/137 |

Primary Examiner—Frank Spear
Attorney, Agent, or Firm—Emrich & Dithmar

[57] ABSTRACT

A system, method and device for continuous mass transfer in fluids, such as blond. A mass transfer device is connected in a closed path between a blood source and a reservoir. Pumps and valves are provided to move the blood through the mass transfer device sequentially in a first path from the blood source to the reservoir and in a second pass from the reservoir to the blood source. Material may be added to the blood flowing from the source. The mass transfer device may be a fractionating device, In that case the system and method may be used for plasma collection, or for displacement of water preparatory to freezing of the blood, or for the formation of washed blood cells from either whole blood or thawed blood. The system and method may be used for hemodialysis, in which case the mass transfer device is a dialyzer.

The fractionating device includes interleaved blood plates and blood fraction collection plates separated by semipermeable membranes. The device is arranged with two separate passages therethrough, each comprising a pair of parallel blood flow channels; the passages being connected in series by external tubing.

23 Claims, 21 Drawing Sheets

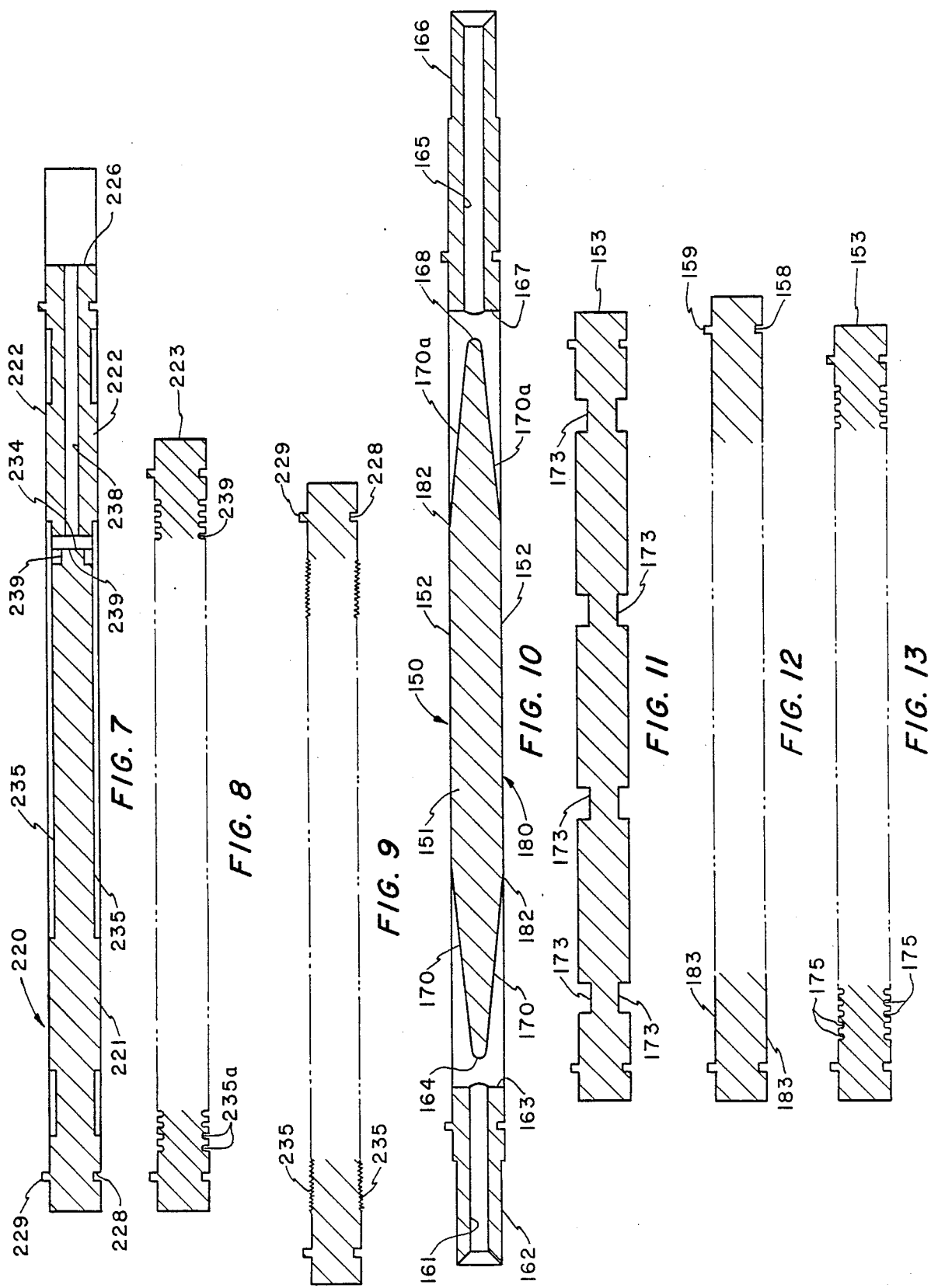

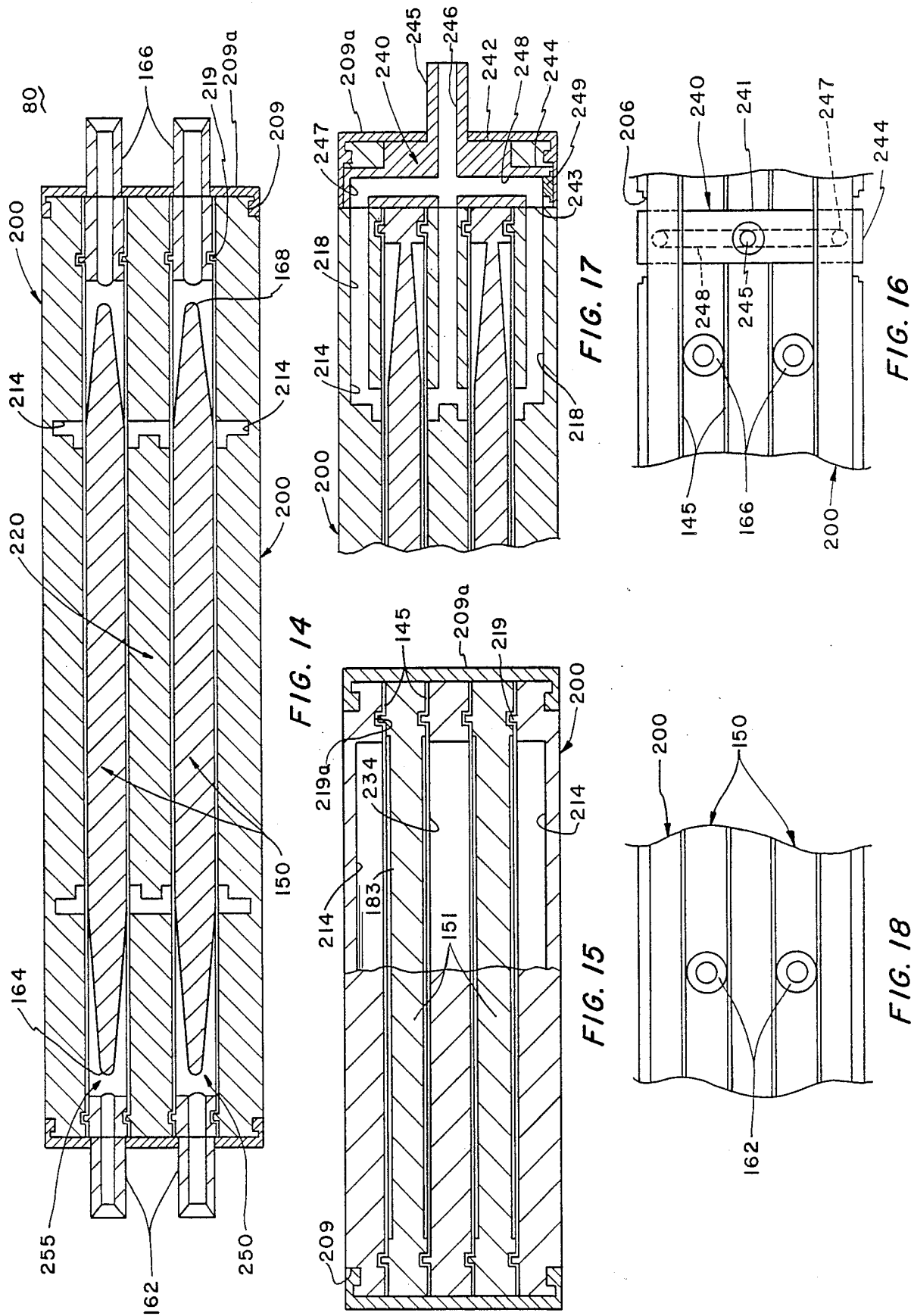

FIRST PASS

FIG. 24 SECOND PASS

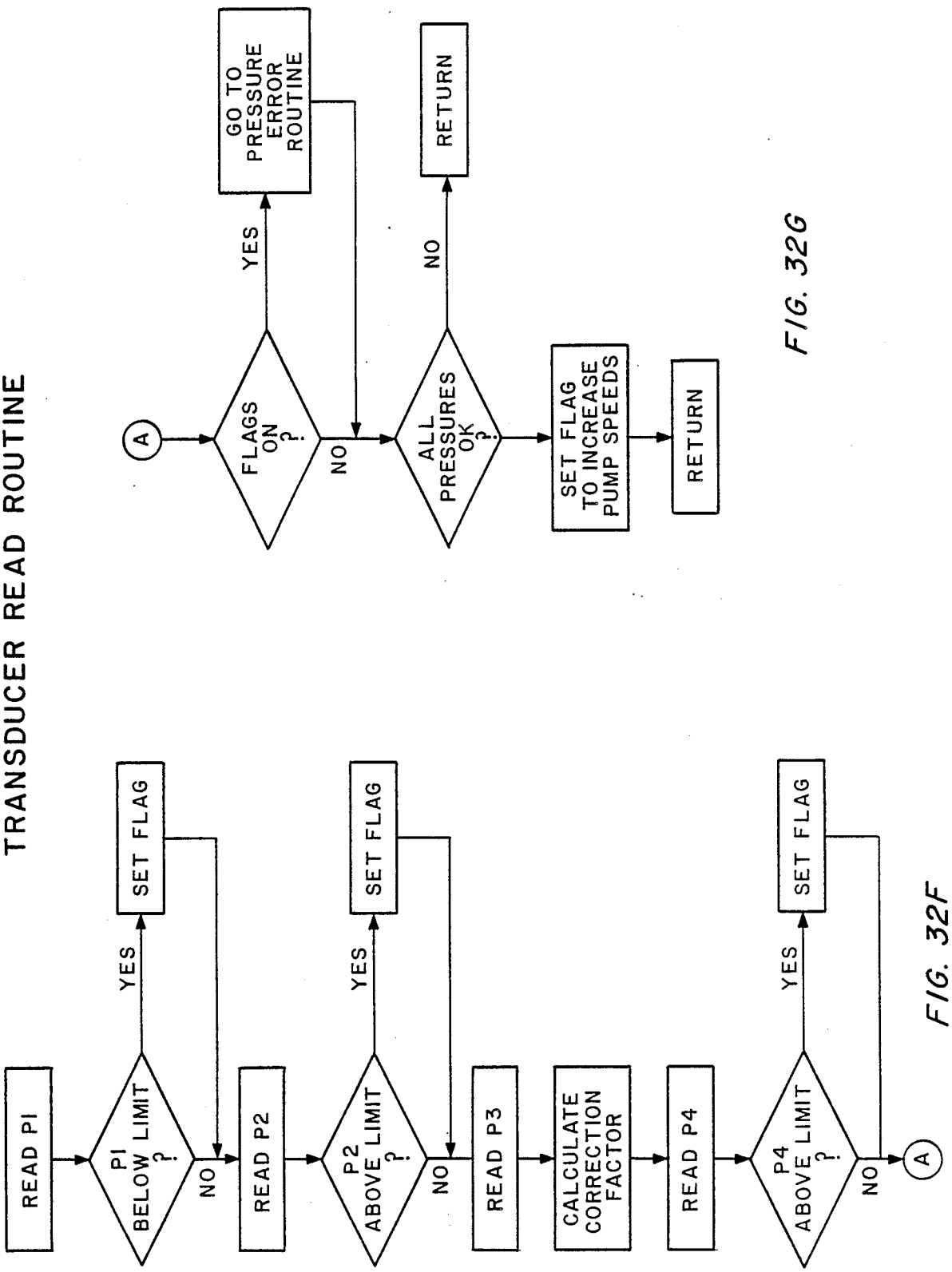

SYSTEM AND METHOD FOR MASS TRANSFER BETWEEN FLUIDS

CROSS REFERENCE TO RELATED APPLICATIONS

This is a continuation-in-part of copending U.S. application Ser. No. 523,007, filed Aug. 15, 1983, and of U.S. application Ser. No. 809,923, filed Dec. 16, 1985 now U.S. Pat. No. 4,898,675.

BACKGROUND OF THE INVENTION

The present invention relates to mass transfer between fluids and, in particular, to mass transfer operations performed on blood. Such mass transfer operations may, for example, include plasmapheresis, hemodialysis, the displacement of water with cryoprotective agents, such as glycerine or ethylene glycol to provide blood for freezing, and the displacement of plasma from whole blood or of cryoprotective agents from thawed blood with saline solution to provide "washed" blood cells.

In the aforementioned copending applications Ser. No. 523,007 and Ser. No. 809,923, applicant has disclosed continuous systems for plasmapheresis, utilizing unique fractionation devices which are highly efficient and compact. Nevertheless, it is always an object to minimize the size of fractionation devices, for reasons of economy of manufacture, to facilitate portability in use and to increase the filtration rate achievable with the device, which is proportional to the length of the flow path through the device. But, in general, further reduction of the size of the device decreases flow rate per unit area. Thus, it is necessary to increase the effective flow rate in order to realize the benefits of increased filtration rate. But the flow rate achievable in continuous loop systems connected to a human donor are limited, since peripheral vein flow in humans is limited to a maximum of 80 to 100 ml/min. Thus, for the particular design of device disclosed in those copending applications, significant size reduction beyond that disclosed was not feasible.

Certain operations, such as plasmapheresis and hemodialysis, are performed on blood as it is received from a human source. In these operations a substance is removed from the blood (plasma in the case of plasmapheresis and blood impurities in the case of hemodialysis), and the remaining constituents are returned to the human source. This typically requires the connection of the apparatus to the human in a closed loop. Originally this was done by the use of two needles inserted into the human, one for withdrawing blood from the human and the other for returning blood to the human. But this is an undesirable arrangement, since most persons dislike having to receive two needles.

It is known to use a double-lumen needle so that only one needle need be used. But this type of needle has given rise to additional problems. In some cases there is insufficient blood flow because the inlet port of the needle becomes occluded by the vein wall. Also, the use of this technique may result in excessive recirculation of blood from the return lumen back into the withdrawal lumen. In the case of plasmapheresis, this may result in undue dilution of the blood by anticoagulant added in the plasmapheresis process.

In the case of hemodialysis, it is also known to utilize a single needle with a single lumen by utilizing valves in the two legs of the tubing loop which lead to and from the needle, and alternately opening and closing these valves, so that blood alternately flows in opposite directions through the needle. But such prior systems have had a number of disadvantages. The system pump runs all the time and, since the blood is flowing from the human source only half the time, the pump must run at twice the normal rate in order to achieve the same flow rates that would be obtained with the two-needle or double-lumen needle approaches. Furthermore, during those times when the valves are configured so that the blood is flowing back to the human, there is no flow from the human, so that, essentially, the pump is operating with an open input. This can result in collapsed input tubing and the creation of air bubbles in the lines which, in turn, necessitates the use of air traps on both sides of the dialyzer. These air traps store a considerable volume of blood and significantly increase the extracorporeal blood volume of the system.

In the case of operations such as blood freezing and washing, which may not require connection to a human donor, the process of displacement of water or cryoprotective agents from the blood is quite time consuming. The rate of addition of saline or cryoprotective agent to the blood cells must be carefully balanced with the rate of removal of water or cryoprotective agent, since otherwise the blood cells are damaged by collapse or expansion. In existing systems, the process of monitoring and regulating the flows are all manually controlled, requiring constant attendance by trained personnel.

SUMMARY OF THE INVENTION

It is a general object of the invention to provide an improved mass transfer system which avoids the disadvantages of prior systems while affording additional structural and operating advantages.

An important feature of the invention is the provision of an improved blood fractionating device which permits size reduction and increased effective flow rate.

In connection with the foregoing feature, it is another feature of the invention to provide a fractionating device which has plural discrete blood flow passages therethrough, which can be interconnected externally of the device.

Another feature of the invention is the provision of an improved plasma collection plate for use in a fractionating device of the type set forth.

In connection with the foregoing features, it is another feature of the invention to provide a plasmapheresis method utilizing a fractionating device of the type set forth, wherein the blood flow passages thereof are connected in series.

In connection with the foregoing feature, yet another feature of the invention is the provision of a plasmapheresis system for performing the method.

It is still another feature of the invention to provide a more efficient method of performing mass transfer operations on blood, wherein the blood is passed through the mass transfer device more than once before being returned to the source.

Another feature of the invention is the provision of a method for performing mass transfer operations on blood, wherein the mass transfer device is coupled to a human source of blood through only a single needle having a single lumen, without significantly increasing the rate at which blood is pumped through the mass transfer device.

In connection with the foregoing features, it is another feature of the invention to provide a method of the type set forth, wherein the mass transfer operation is plasmapheresis.

Still another feature of the invention is the provision of a method of the type set forth wherein the mass transfer operation performed is hemodialysis.

Yet another feature of the invention of the invention is the provision of a system for performing the foregoing methods.

Yet another feature of the invention is the provision of an improved fractionating device for performing certain of the foregoing methods.

Certain of these features are attained by providing a device for continuously producing a blood fraction, comprising a stack of alternating plates and semi-permeable membranes, the membranes being selectively permeable to the blood fraction, the plates including at least two blood flow channels and at least two collection channels therein, the blood flow channels respectively facing the collection channels and being respectively separated therefrom by the semi-permeable membranes, two blood inlets and two blood outlets respectively communicating with the blood flow channels to establish two separate longitudinally extending blood flow passages, each blood flow channel having a transfer portion extending longitudinally of the passage, each collection channel having a collection portion disposed substantially in registry with the transfer portion of the facing blood flow channel for receiving the blood fraction passing through the associated one of the membranes, and a fraction outlet for conducting the blood fraction from each of the collection channels, whereby the blood fraction continuously transfers from blood passing through the transfer portions of the blood flow channels through the membranes into the adjacent collection channels and to the fraction outlet.

Other features of the invention are attained by providing a plate for collecting plasma comprising: a body having a pair of substantially opposed surfaces with at least one of the surfaces having a plasma collection channel therein, an outlet in fluid communication with the plasma collection channel, the plasma collection channel having a longitudinally extending collection portion and a transversely extending slot at the end of the collection portion in communication therewith and a combining portion for conducting blood from the slot to the outlet, the slot having a greater depth than the collection portion of the channel, the combining portion comprising a multiple bifurcated manifold.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there are illustrated in the accompanying drawings preferred embodiments thereof, from an inspection of which, when considered in connection with the following description, the invention, its construction and operation, and many of its advantages should be readily understood and appreciated.

FIG. 7 is a view in vertical section taken along the lines 7—7 in FIG. 6;

FIG. 8 is a view in vertical section taken along the line 8—8 in FIG. 6;

FIG. 9 is a view in vertical section taken along the line 9—9 in FIG. 6;

FIG. 10 is a view in vertical section taken along the line 10—10 in FIG. 5;

FIG. 11 is a view in vertical section taken along the line 11—11 in FIG. 5;

FIG. 12 is a view in vertical section taken along the line 12—12 in FIG. 5;

FIG. 13 is a view in vertical section taken along the line 13—13 in FIG. 5;

FIG. 14 is an enlarged view in vertical section taken along the line 14—14 in FIG. 2, and showing the plastic clamping ring;

FIG. 15 is an enlarged view in vertical section taken along the line 15—15 in FIG. 2, and showing the plastic changing ring;

FIG. 16 is an enlarged fragmentary end elevational view of the fractionating device of FIG. 2, as viewed from the right-hand thereof;

FIG. 17 is an enlarged fragmentary view in vertical section taken along the line 17—17 in FIG. 2, and showing the plastic clamping ring;

FIG. 18 is an enlarged fragmentary end elevational view of the fractionating device of FIG. 2, as viewed from the left-hand end thereof;

FIGS. 32A–32G are a flow diagram of the computer program for the system of FIG. 1.

DESCRIPTION OF THE PREFERRED EMBODIMENTS

Figure 1:
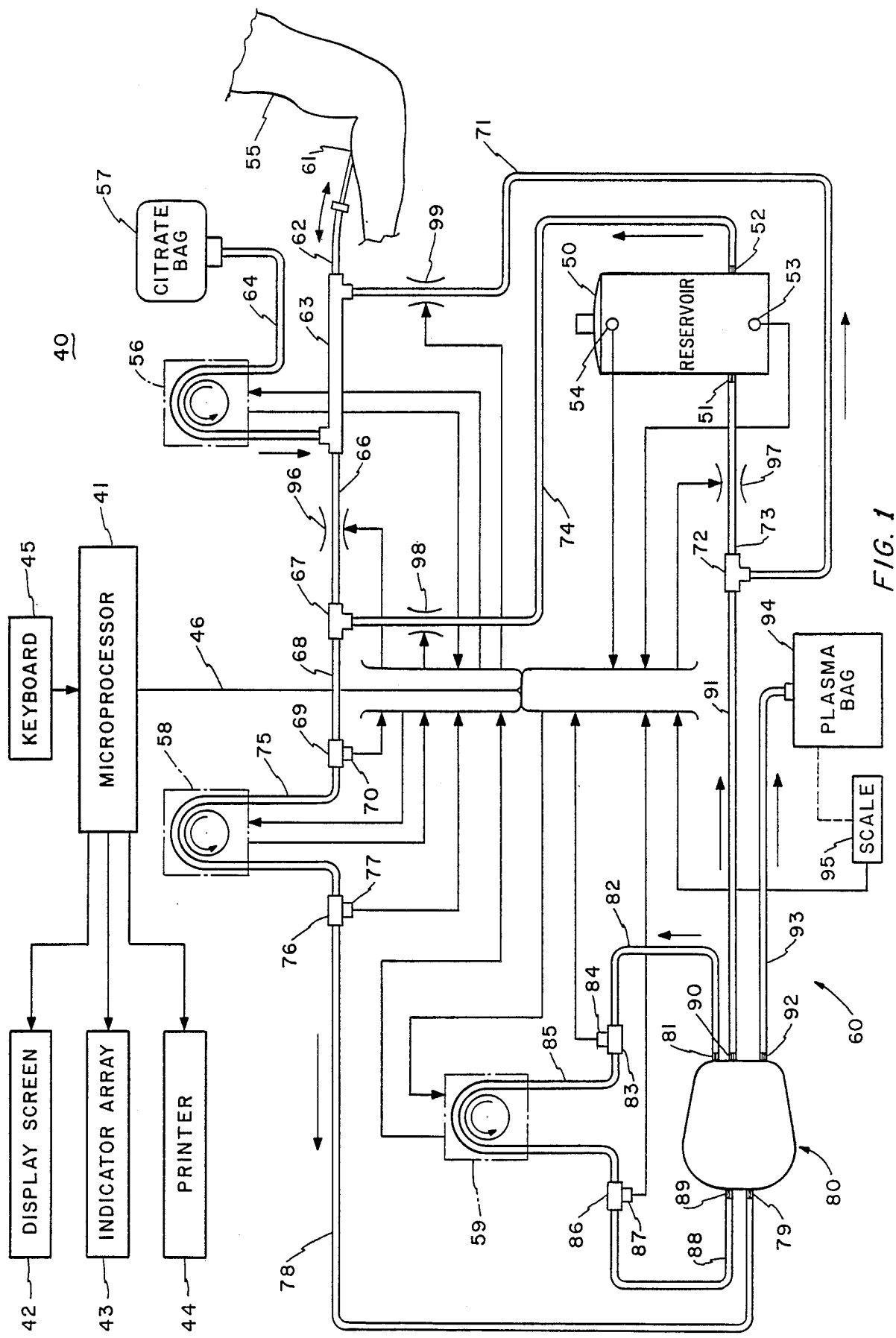
FIG. 1 is a diagrammatic view of an automatic system in accordance with the present invention, including a fractionating device constructed in accordance with the present invention, the system being arranged for performing a plasmapheresis method in accordance with the present invention wherein the method is customized for individual donors.

Referring now to FIG. 1, there is illustrated an automated blood fractionating system, generally designated by the numeral 40. The system 40 includes a microprocessor 41 coupled to a display screen 42, an indicator array 43 and a printer 44 for outputting information from the microprocessor 301. The system 300 also includes a keyboard 45 coupled to the microprocessor 41 for inputting information thereto. The microprocessor 41 is coupled to the mechanical parts of the system 40 by a multi-conductor cable 46 for receiving information therefrom and for controlling the operations thereof.

It is a significant aspect of the present invention that the system 40 includes a reservoir 50 having an inlet 51 and an outlet 52. The reservoir 50 is also provided with lower and upper fluid level sensors 53 and 54, which respectively produce electrical output signals when the level of fluid in the reservoir 50 reaches predetermined lower and upper limits. Blood is provided to the system 40 by an associated blood source, such as a donor 55. The system 40 also includes an anticoagulant pump 56 for pumping anticoagulant from an associated source, such as a citrate bag 57. The system 40 also includes blood pumps 58 and 59 for moving blood between the donor 55 and the reservoir 50 through a disposable fractionator unit 60, which includes a fractionator 80 and associated tubing for interconnecting the donor 55, the reservoir 50 and the fractionator 80 in a closed path. The pumps 56, 58 and 59 may be peristaltic roller pumps of the type disclosed in U.S. Pat. No. 4,568,255.

Figure 21:
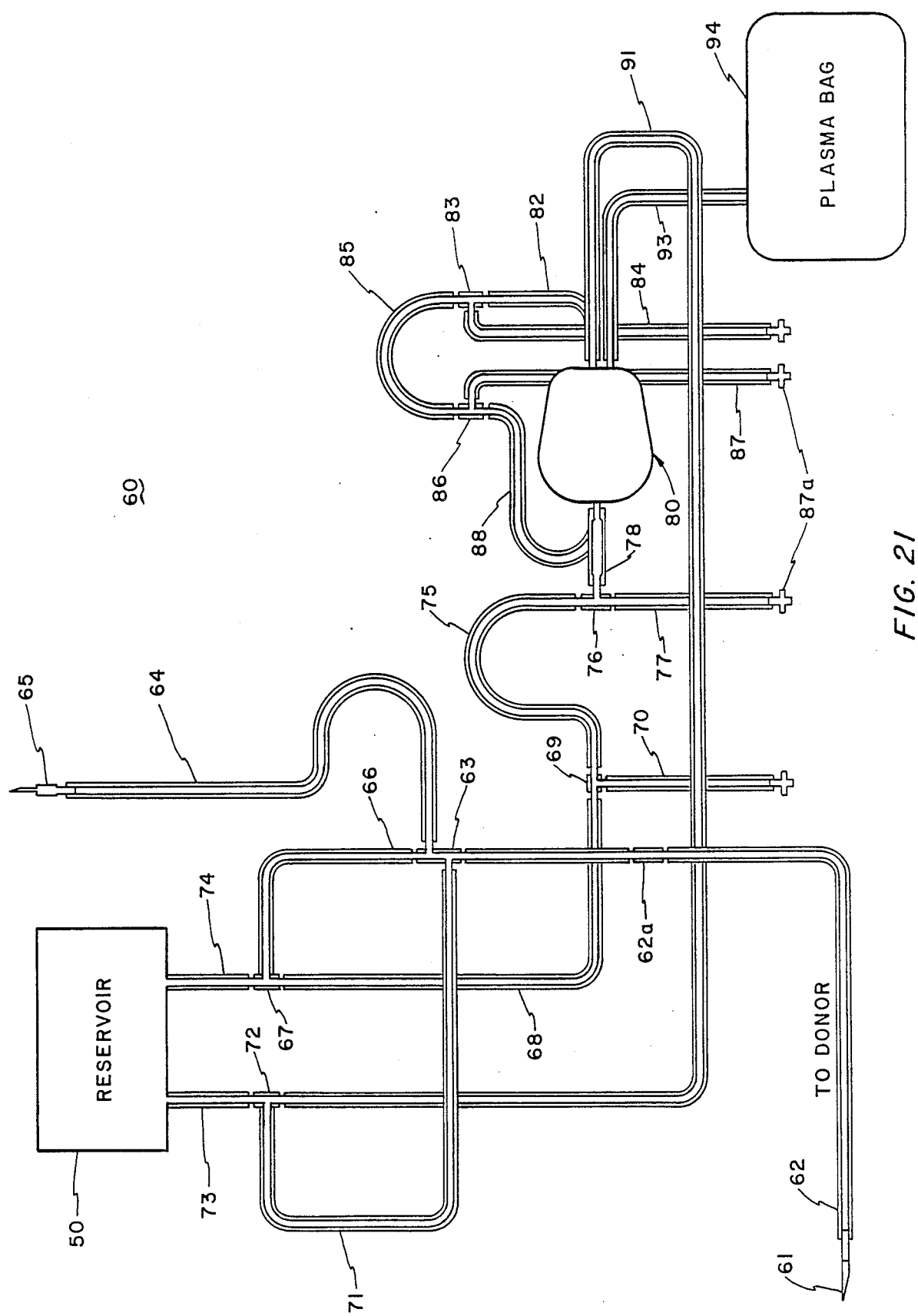
FIG. 21 is a plan view of the disposable parts of the system of FIG. 1.

Referring also to FIG. 21, the disposable fractionator unit 60 includes a catheter or single lumen needle 61 adapted to be inserted into a blood vessel in the arm of the donor 55. The needle 61 is coupled by a tube 62 to one port of a four-port mixing chamber 63, a second port of which is coupled to a citrate tube 64 provided at its free end with a spike 65 for insertion into the citrate bag 57. A bubble detector 62a may be provided in the tube 62. A third port of the mixing chamber 63 is coupled by a tube 66 to one arm of a T-fitting 67, another arm of which is coupled by a tube 68 to a pressure fitting 69 which has a monitoring port coupled to one end of a pressure line 70.

The fourth port of the mixing chamber 63 is coupled by a tube 71 to one arm of a T-fitting 72, another arm of which is coupled by a tube 73 to the inlet 51 of the reservoir 50. The outlet 52 of the reservoir 50 is coupled by a tube 74 to another arm of the T-fitting 67. The pressure fitting 69 is coupled by a tube 75 to a pressure fitting 76, which has a monitoring port coupled to one end of a pressure line 77. The pressure fitting 76 is, in turn, coupled by a tube 78 to a first inlet 79 of the fractionator 80, which also has a corresponding first outlet 81, coupled by a tube 82 to a pressure fitting 83 provided with a monitoring port coupled to one end of a pressure line 84. The pressure fitting 83 is also coupled by a tube 85 to a pressure fitting 86, which is provided with a monitoring port coupled to one end of a pressure line 87. The tubes 75 and 85 are adapted in use to be respectively disposed through the blood pumps 58 and 59.

Each of the pressure lines 70, 77, 84 and 87 is shown to scale in FIG. 21 and in diagrammatic form in FIG. 1, and is provided at its distal end with a Luer connector 87a (FIG. 21). The pressure fitting 86 is coupled by a tube 88 to a second inlet 89 of the fractionator 80, a corresponding second outlet 90 of which is coupled by a tube 91 to another arm of the T-fitting 72. The fractionator 80 is also provided with a plasma outlet 92 which is coupled by a tube 93 to a plasma bag 94. The system 40 is also provided with a scale 95 for weighing the contents of the plasma bag 94, and with four clamp-type valves 96, 97, 98 and 99 (FIG. 1).

Figure 19:
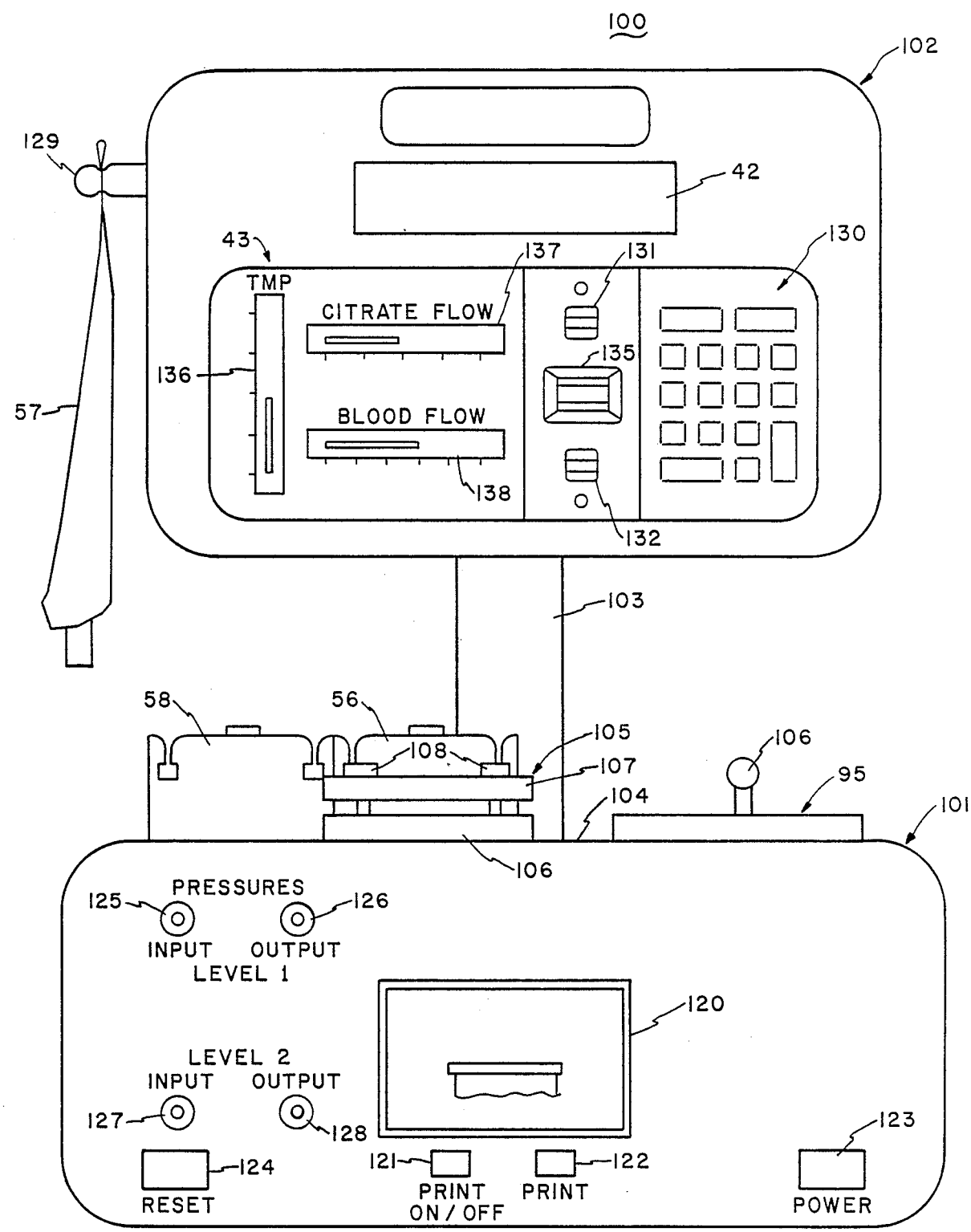
FIG. 19 is a front elevational view of the console unit of the system of FIG. 1.
Figure 20:
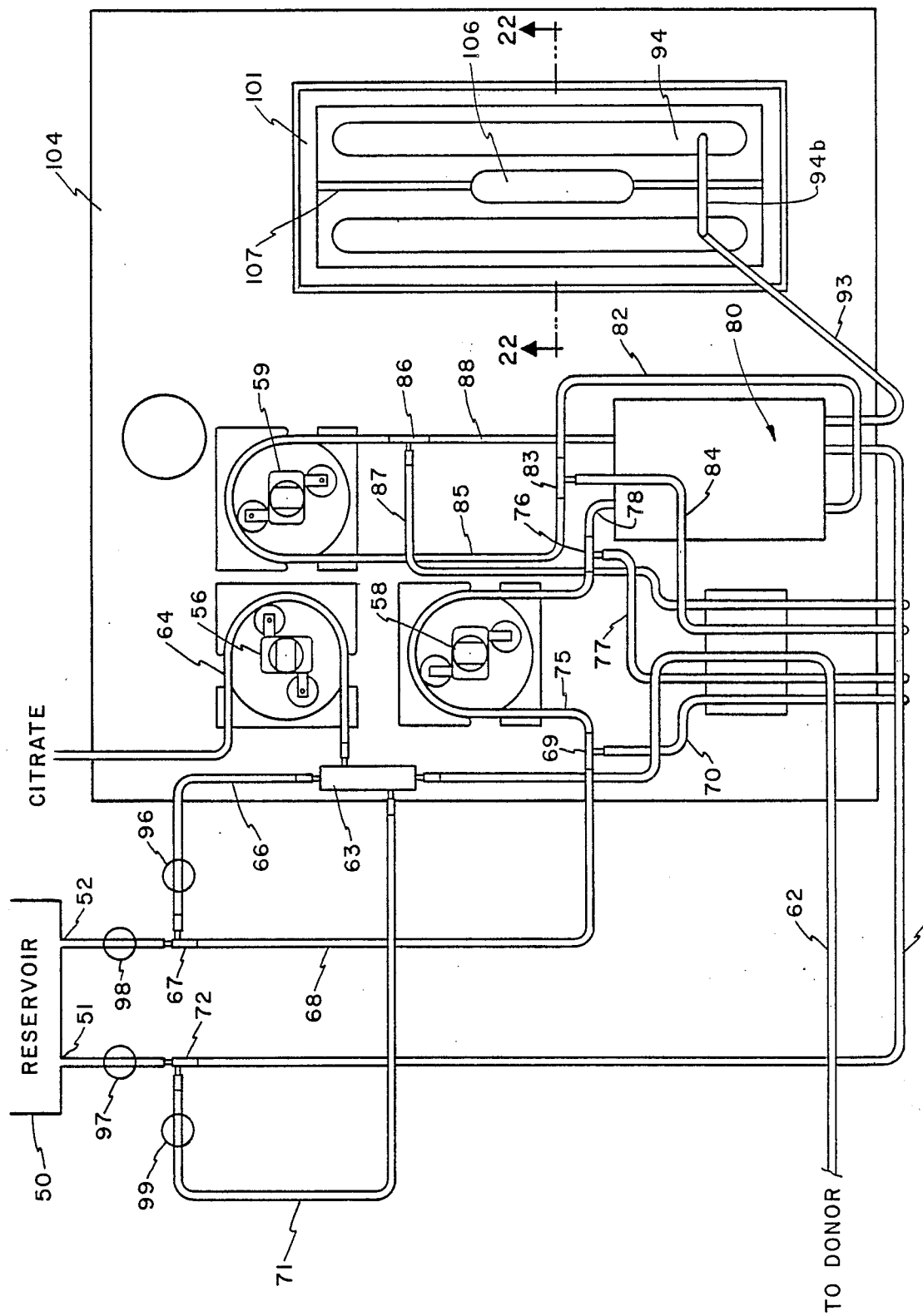
FIG. 20 is a top plan view of the lower housing of the console unit of FIG. 19 with disposable parts in place.

Referring also to FIGS. 19 and 20, the system 40 includes a console unit 100 which may be generally of the type shown in U.S. Pat. No. Des. 289,548. The console unit 100 includes a lower box-like housing 101 and an upper box-like housing 102 mounted above the rear end of the lower housing 101 by means of a vertical support post 103. Preferably, the printer 44, the scale 95, motors for the pumps 56, 58 and 59, a power supply, and pressure transducers are all mounted within the lower housing 101, while the pumps 56, 58 and 59 are mounted on the top wall 104 of the lower housing 101 externally thereof. The microprocessor 41, the display screen 42, the indicator array 43 and keyboard 45 are all mounted in the upper housing 102, interconnections between the lower and upper housings 101 and 102 being provided through the support post 103, which may be hollow.

Also mounted on the top wall 104 of the lower housing 101 is a fractionator holder 105 (FIG. 19), which includes a lower plate 106 fixedly secured to the top wall 104 and an upper plate 107 which is disposable above the lower plate 106 for cooperation therewith to clamp the fractionator 80 therebetween, the parts being secured in place by fasteners 108. Formed in the top wall 104 of the lower housing 101 is a large rectangular opening 109 (see FIG. 22), in which the scale 95 is mounted. The scale 95 includes a receptacle 110 which is generally in the form of an open-top rectangular box. Integral with the side walls of the receptacle 110 at the upper end thereof and extending laterally outwardly therefrom substantially perpendicular thereto around the entire perimeter thereof is a support flange 111, which is provided at its outer edge with a depending retaining flange 112 extending around the entire circumference thereof.

In use, the receptacle 110 fits in the opening 109 with the support flange 111 overlying the upper edge of an upstanding lip 113 on the lower housing top wall 104 around the entire perimeter of the opening 109. It will be appreciated that the retaining flange 112 cooperates with the lip 113 to provide a splash proof interlock to prevent any loose liquid in the receptacle 110 from falling through the opening 109. As can be seen in FIG.

22, the receptacle 110 is suspended above the lip 113, being resiliently supported in any suitable manner on the scale 95. The bottom wall of the receptacle 110 is provided with a depending rectangular clamp well 114, the upper end of which is widened as at 115. A clamp 116 is adapted to be disposed in the clamp well 114, and includes a rectangular main plate 117, the lower end of which carries a pair of pivoting wings 118, respectively disposed on the opposite sides of the main plate 117. Each wing 118 carries at its distal end a gripping bead 119, substantially circular in transverse cross section. The receptacle 110 and the clamp 116 may be of the type disclosed in U.S. Pat. No. 4,592,582.

Figure 22:
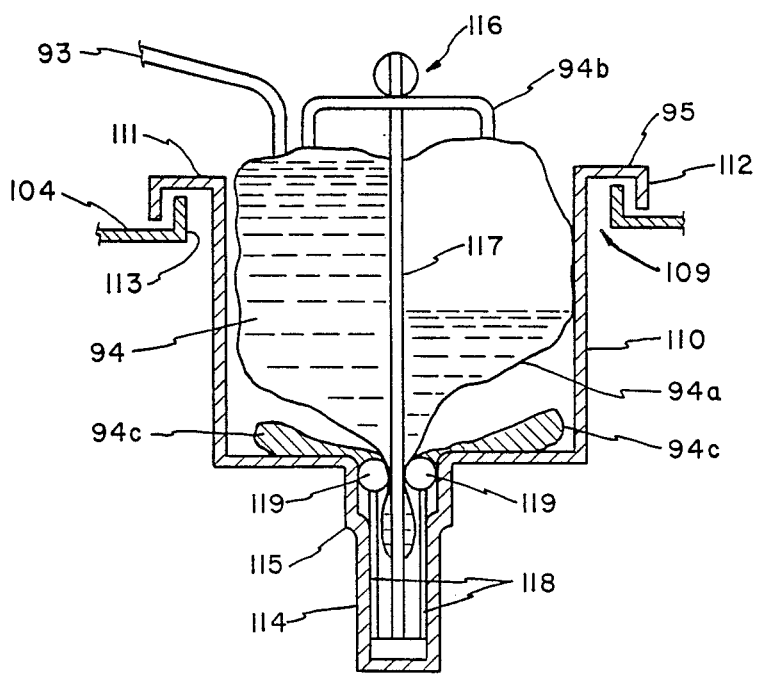
FIG. 22 is an enlarged fragmentary view in vertical section taken along the line 22—22 in FIG. 20, with plasma bags in place.

The plasma bag 94 may be of the type illustrated in FIG. 22, and will preferably be packaged with a second bag 94a, which may be needed for donors weighing over 167 pounds. The second bag 94a has a spike assembly including a tube 94b adapted to be coupled to a nipple in the bag 94 to provide an overflow connection between the bags 94 and 94a when both are used. It will be appreciated that the disposable fractionator unit 60, which includes all of the structure in FIG. 21, is preassembled as a unit and, after use, the plasma bag 94 and/or 94a may be separated and the remainder of the fractionator unit 60 may be disposed of.

In use, the plasma bags 94 and 94a are respectively disposed on opposite sides of the main plate 117. Each bag is folded in half and the folds 94c are inserted between the main plate 117 and wings 118, which are then pivoted up for cooperation with the main plate 117 to clamp therebetween the folds 94c. Then the clamp 116 is inserted in the clamp well 114, which is dimensioned so that the gripping beads 119 are interference fitted in the widened upper end 115 of the well 114, with the wings 118 being disposed snugly along the inner surfaces of the well 114.

Referring now to FIG. 19, the front wall of the lower housing 101 is provided with a printer output 120 which may emit a printed paper tape, or the like.

Also mounted on this front panel are an ON-OFF switch button 121 and a control switch button 122 for the printer, as well as a power switch button 123 and a reset switch button 124 for the system 40. Also mounted on this panel are Luer connectors 125, 126, 127 and 128 for respectively receiving the connectors 87a of the pressure lines 70, 77, 84 and 87, the connectors 125-128 being coupled to suitable pressure sensors PS (see FIGS. 23 and 24) inside the lower housing 101.

The upper housing 102 carries on its side wall a bag holder 129 on which the citrate bag 57 can be hung. Mounted in suitable openings in the front panel of the upper housing 102 for viewing and access by a user are the keyboard 45, the display screen 42 and the indicator array 43. The keyboard 45 includes a key pad 130 as well as a START switch 131 and a STOP switch 132. The indicator array 43 includes an alarm indicator light 135, as well as a pressure gauge 136, an anticoagulant flow gauge 137 and a blood flow gauge 138. The pressure gauge 136 registers the so-called "trans-membrane pressure", i.e., the pressure at the inlet of the fractionator 80, as detected by the sensors PS coupled to the Luer connections 125-128.

Figure 2:
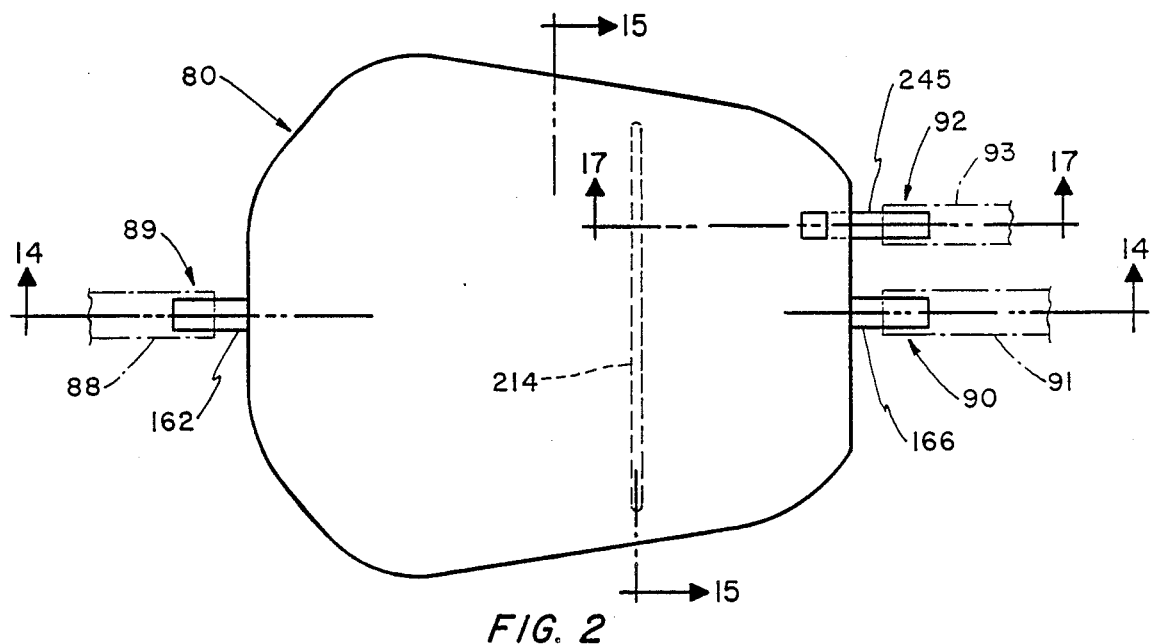
FIG. 2 is an enlarged top plan view of the blood fractionating device illustrated in FIG. 1.
Figure 3:
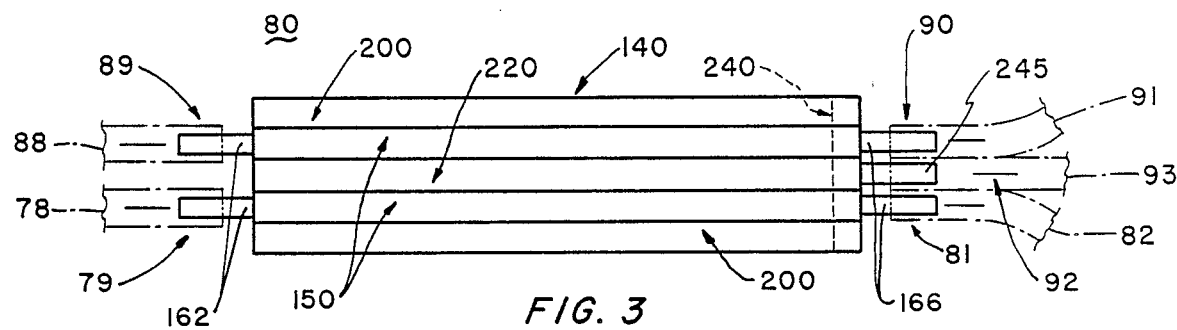
FIG. 3 is a side elevational view of the device illustrated in FIG. 2.

Referring now to FIGS. 2-18, the blood fractionator 80 is made up of a stack 140 of plates, there being provided two external blood fraction collection plates 200, two internal double-sided blood plates 150 and an interior or internal double-sided blood fraction collection plate 220, as well as a blood fraction outlet manifold 240, with adjacent ones of the blood fraction collection plates and blood plates being separated by appropriate semipermeable membranes 145. As illustrated, the blood fractionator 80 is comprised of a stack 140 of five separate plates and four membranes 145 interleaved between the plates such that each blood fraction collection plate 200, 220 faces a blood plate 150 and is separated therefrom by an appropriate membrane 145. It will be appreciated that the stack 140 could as easily be comprised of a stack of plates in which the external plates are blood plates, and including two double-sided blood-fraction collection plates separated by an internal double-sided blood plate. The number of plates also could be increased. It will be noted that the fractionator 80 is shown diagrammatically in FIG. 1, and the inlets and outlets are shown spread out so that they can be seen, their actual positions being illustrated in FIGS. 2 and 3.

Referring now in particular to FIGS. 4, 5, and 11-13, the blood plates 150 are substantially identical in construction, each being provided with the same configuration on both sides thereof. Accordingly, only one side will be described for the sake of brevity. Each of the blood plates 150 includes a body 151 having flat side surfaces 152 interconnected by an opposed peripheral edge surface 153, which intersects the side surfaces 152 at substantially right angles thereto. The body 151 is generally oblong in shape, having a large inlet end 154 and a small outlet end 155. A rectangular notch 156 is formed in the peripheral edge surface 153 at the small outlet end 155 and extends throughout the entire thickness of the body 151 between the flat side surfaces 152. Formed in one of the flat side surfaces 152 and extending around the periphery thereof is a recess or groove 158 (FIGS. 11 and 12). Projecting from the other side surface 152 of the blood plate 150 around the periphery thereof, substantially perpendicular thereto, is a tongue or ridge 159.

Figure 5:
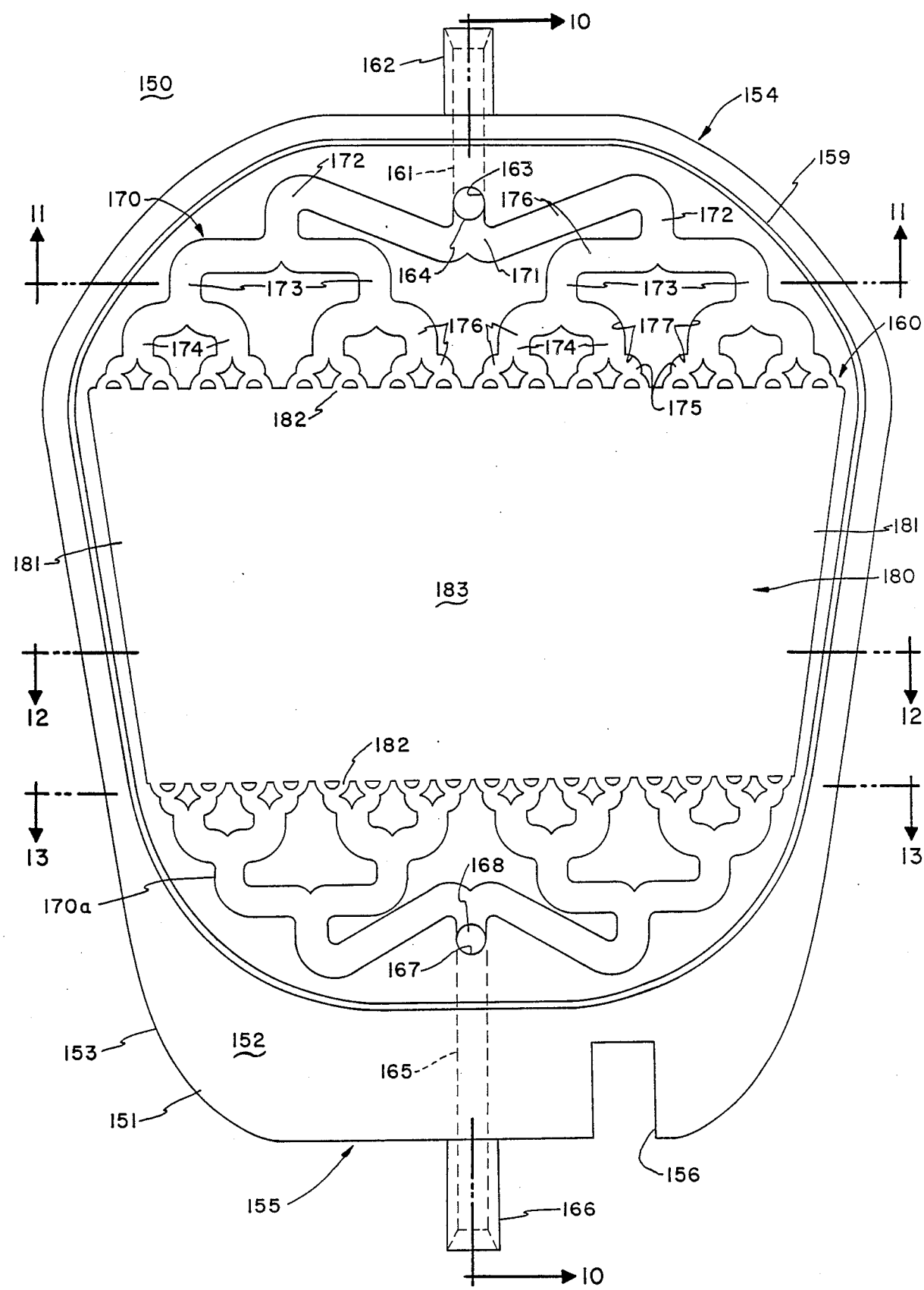
FIG. 5 is an enlarged plan view of a blood plate of the fractionating device of FIGS. 2-4.
Figure 6:
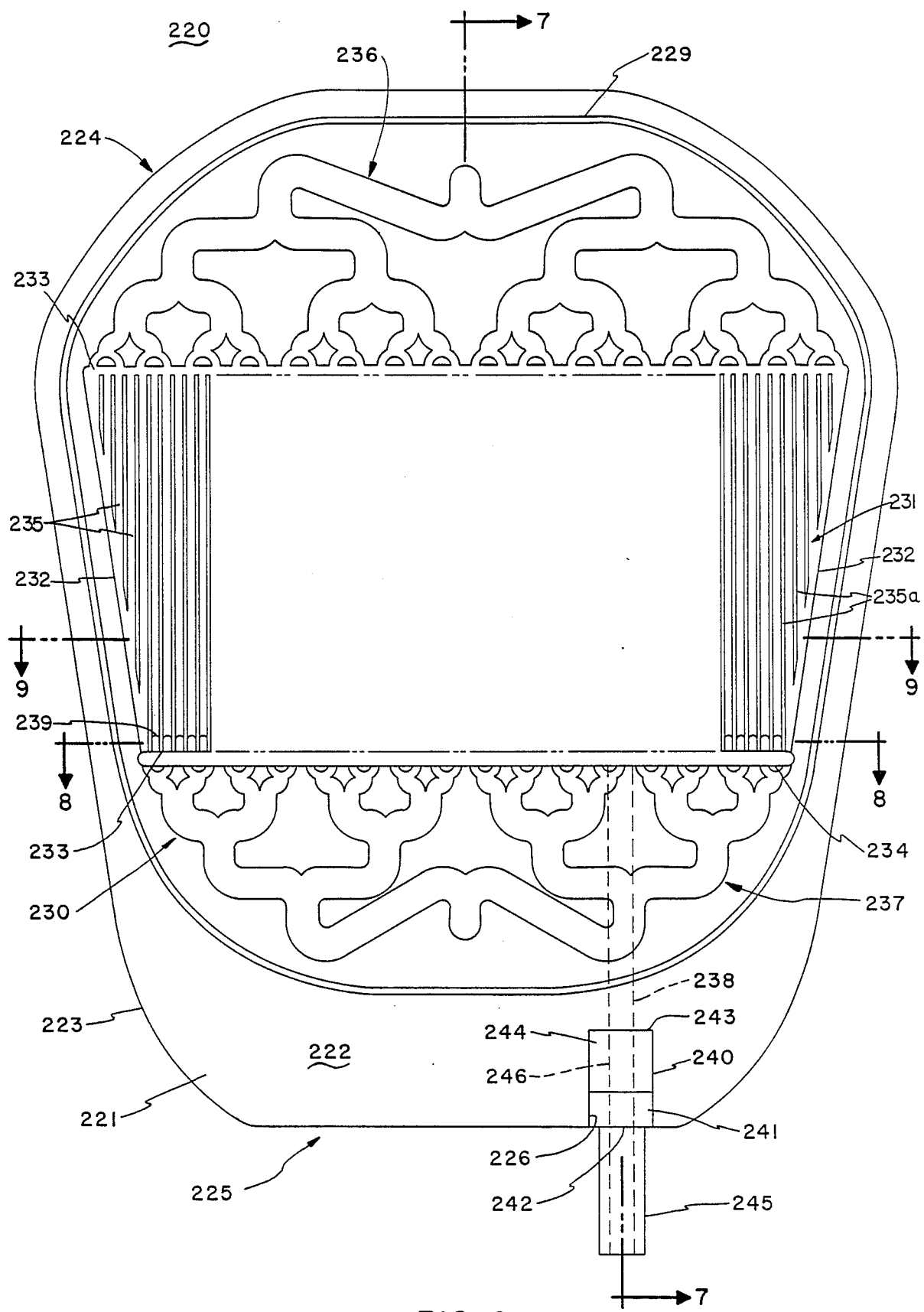
FIG. 6 is an enlarged plan view of an internal blood fraction collection plate of the fractionating device of FIGS. 2-4.

Formed in each of the side surfaces 152 is a blood flow channel generally designated by the numeral 160, which includes a distribution portion 170, a combining portion 170a and a transfer portion 180. Formed in the body 151 at the large inlet end 154 thereof, and extending longitudinally thereof is a cylindrical inlet bore 161, communicating at its outer end with an inlet tube 162 which is fixed to the body 151 and projects longitudinally outwardly therefrom. The inlet bore 161 communicates at its inner end with a transverse bore 163 which extends transversely between the opposed flat side surfaces 152. The transverse bore 163 has an inside splitter surface 164 for dividing the incoming flow and directing it to both sides of the body 151. The splitter surface 164 is rounded to prevent contact of the blood flowing therethrough with a sharp edge, for a purpose to be explained more fully below (FIG. 5). Similarly, there is formed in the edge surface 153 at the small outlet end 155 of the body 151 a cylindrical outlet bore 165 which extends substantially coaxially with the inlet bore 161. The outlet bore 165 communicates at its outer end with an outlet tube 166 which is fixed to the body 151 and projects longitudinally outwardly therefrom. The outlet bore 165 communicates at its inner end with a transverse bore 167 extending between the flat side surfaces 152 and having a rounded inside facing surface 168.

The distribution portion 170 and the combining portion 170a are each in the form of a multiple bifurcated manifold, with five sets of bifurcations. Referring to the distribution portion 170, the single blood stream flowing through the inlet tube 161 is divided into 32 blood streams, as hereinafter set forth, at the delivery end of the manifold 170. More specifically, the manifold is substantially the same as that disclosed in the aforementioned copending U.S. application Ser. Nos. 523,007 and 809,923. Blood flowing through the inlet bore 161 passes into the transverse bore 163, which carries it to the distribution manifolds 170 on each side of the blood plate 150. More particularly, in each manifold 170, the blood flows from the transverse bore 163 into a main longitudinal channel 171, which then splits into two lateral channels 176, which respectively flow into second tier longitudinal channels 172, which are in turn bifurcated into lateral channels 176 which lead to third tier longitudinal channels 173. The bifurcation continuing to fourth tier longitudinal channels 174 and fifth tier longitudinal channels 175, the longitudinal channels of each tier being interconnected by lateral channels 176. Each of the channels 171 through 176 has rounded portions 177 at the juncture thereof with intersecting channels so as to prevent the impingement of the blood into corners which results in stagnation and less smooth distribution and flow. Each of the fifth tier longitudinal channels 175 has an entrance into the transfer portion 180 of the blood flow channel 160, there being 32 such entrances.

As can best be seen in FIG. 10 (a composite section which follows the tiers of the manifolds 170 and 170a), the bifurcated manifolds 170 and 170a have a continuously changing depth, with the manifolds being deeper at the transverse bores 163 and 167 and being shallower at the junctures with the transfer portion 180. It is preferred that this gradation in depth be uniform so that the depth of the manifolds 170 and 170a will be the same along a plane transverse to the longitudinally established flow path through the blood plate 150. Preferably, the varying depth of the manifolds 170 and 170a is such that the depth of the manifolds at their junctures with the transfer portion 180 is exactly the same as the depth of the transfer portion 180.

The transfer portion 180 is generally trapezoidal in plan view and is defined by side edges 181 and end edges 182 with a generally flat uniformly deep surface 183 which is shallow and, as hereinbefore set forth, is of the same depth as the entrances from both of the distribution and collection manifolds 170 and 170a. The depth of the surface 183 below the level of the associated side surface 152, is too small to be clearly visible at the scale of the drawings. Because the transfer portion 180 of the blood flow channel 160 is trapezoidal in shape, i.e., it tapers form the inlet end 154 to the outlet end 155 of the blood plate 150, the transverse dimension of the combining manifold 170a is less than the transverse dimension of the distribution manifold 170. However, the configuration of the combining manifold 170a is precisely the same as the configuration of the distribution manifold 170. Therefore, like numerals have been placed on like portions to prevent repetitive description. In other words, the entrances of the combining manifold 170a at the outlet end of the transfer portion 180 are identical in configuration and number but smaller in overall transverse dimension than the entrances into the transfer portion 180 from the distribution manifold 170.

Figure 4:
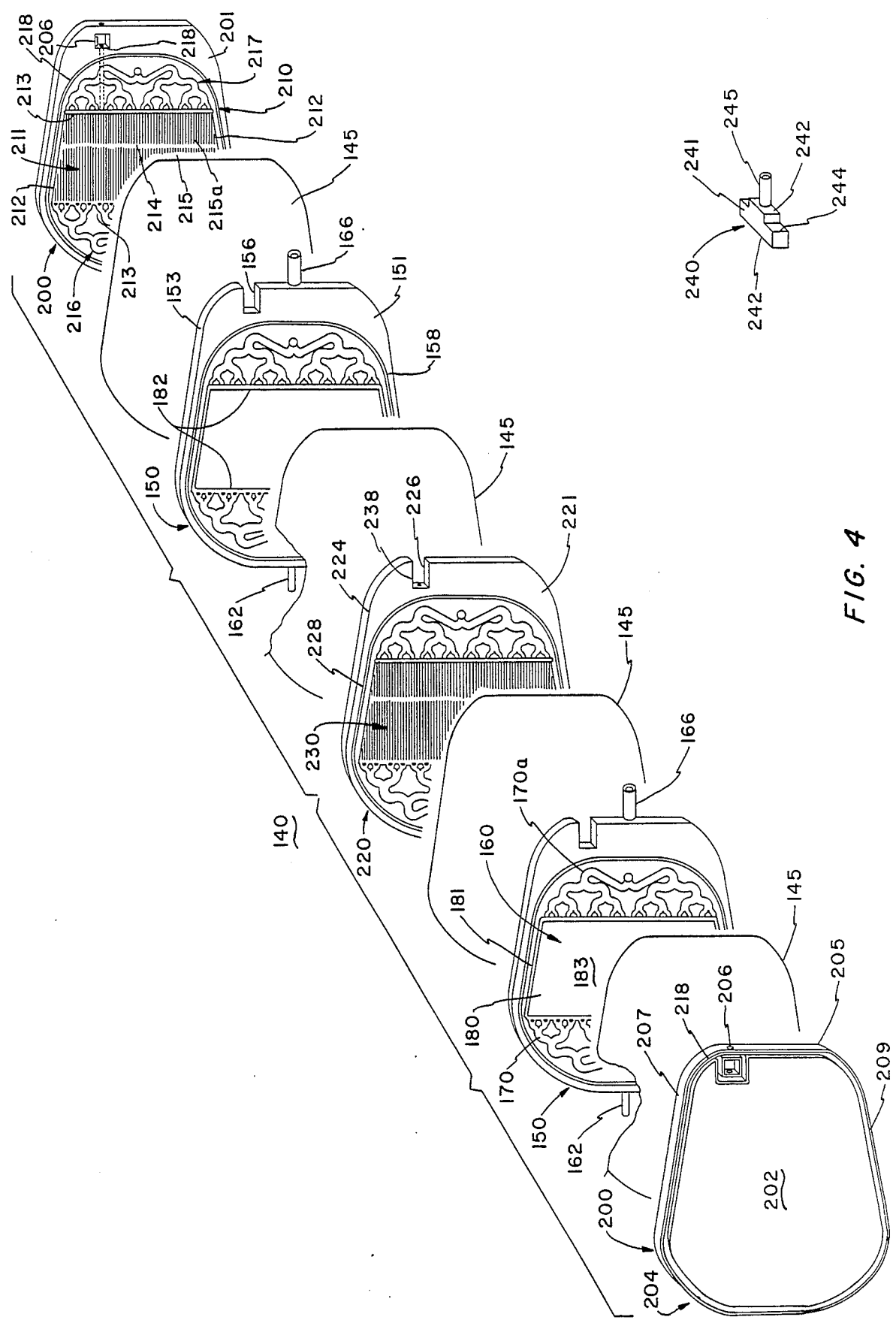
FIG. 4 is an exploded perspective view of the blood fractionating device of FIG. 2.

Referring to FIG. 4, the external blood fraction collection plates 200, though not identical, are mirror images of one another and, for the sake of brevity, like numbers have been placed on like portions of each of the plates 200. Each of the blood fraction collection plates 200 includes a body 201 which is generally oblong in shape and has an outer flat surface 202 opposed by an inner flat surface 203. The plate 200 has a large inlet end 204 and a small outlet end 205, and a rectangular slot 206 extending therethrough between the outer and inner surfaces 202 and 203 adjacent to the small outlet end 205. The outer and inner surfaces 202 and 203 are disposed substantially parallel to each other and are interconnected around the entire periphery thereof by a normal peripheral surface 207. The outer surface 202 of the plate 200 has a peripheral groove 209 therein for a purpose to be explained more fully below.

Each of the external blood fraction collection plates 200 has, on the inner flat surface 203 thereof, a blood fraction collection channel 210 which has a generally trapezoidal collection portion 211 defined by side edges 212 and end edges 213. At the end of the collection portion 211 toward the small outlet end 205 of the plate 200 is a transversely extending groove 214 formed in the inner surface 203 and disposed in fluid communication with a plurality of longitudinally extending shallow collection grooves 215 separated by ridges 215a and extending the length of the collection portion 211. As is hereinafter explained (see FIGS. 14 and 17), the groove 214 is substantially deeper than the shallow collection grooves 215 and the portion of the collection grooves 215 adjacent to the transverse groove 214 is deeper than the remainder of the shallow grooves 215 but shallower than the transverse groove 214. The end of the collection portion 211 adjacent to the large inlet end 204 of the plate 200 communicates with the 32 delivery ports of a multiple bifurcated manifold 216 and, similarly, the transverse groove 214 communicates with a multiple bifurcated manifold 217. The manifolds 216 and 217 are, respectively, substantially identical to the manifolds 170 and 170a of the blood plates 150, except that the depths of the manifolds 216 and 217 do not vary. The transverse groove 214 communicates with one end of a longitudinally extending cylindrical blood fraction outlet bore 218, the other end of which communicates with the rectangular slot 206. A tongue or ridge 219 surrounds the blood fraction collection channel 210 and projects perpendicularly from the inner flat surface 203 of one of the blood fraction collection plates 200, while the other one of the plates 200 has a complementary groove 219a formed in the inner flat surface 203 thereof (see FIGS. 14 and 15).

Referring now to FIGS. 6-9, there is shown the internal blood fraction collection plate 220, which has the same configuration on both sides of the plate. The plate 220 includes a body 221 which is generally oblong in shape and has opposed flat surfaces 222 interconnected by a peripheral edge surface 223 disposed substantially perpendicular thereto. The body 221 has a large end 224 and a small end 225, in which is formed a rectangular notch 226, of substantially the same size and configuration as the notches 156 in the blood plates 150. One of the flat surfaces 222 has a groove 228 formed therein extending around the periphery thereof, and the flat surface 222 has a tongue or ridge 229 projecting perpendicularly therefrom around the periphery thereof, the groove 228 and the ridge 229 being respectively complementary to the ridges 159 and grooves 158 on the blood plates 150 which are, in turn, complementary to the ridge 219 and the groove 219a of the external blood fraction collection plates 200.

Respectively formed in the opposed flat surfaces 222 are blood fraction collection channels 230 which are mirror images of each other and are substantially identical to blood fraction collection channels formed in the external blood fraction collection plates 200. More particularly, each of the blood fraction collection channels 230 has a trapezoidal collection portion 231 defined by side edges 232 and end edges 233. The blood fraction collection channel 230 also includes a transverse slot 234 which extends entirely through the plate 220 and opens onto both of the opposed flat surfaces 222 at the small ends of the collection portions 231. The collection portion 231 has a plurality of longitudinally extending shallow collection grooves 235 separated by ridges 235a. Immediately adjacent the transversely extending slot 234 and communicating therewith are portions 239 of the grooves 235 which are deeper than the remainder of the grooves 235.

The blood fraction collection channel also includes multiple bifurcated manifolds 236 and 237, respectively disposed at the large and small ends of the plate 220 and respectively substantially identical to the manifolds 216 and 217 in the external plates 200. The manifold 236 has 32 openings which communicate with the large end of the trapezoidal collection portion 231 and the manifold 237 has 32 openings which communicate with the transverse slot 234. Also formed in the body 221 is a longitudinally extending cylindrical blood fraction outlet bore 238, which has one end thereof communicating with the transverse slot 234 and the other end thereof communicating with the bottom of the notch 226.

The membranes 145 are selected so that the pore size thereof selectively passes the blood fraction to be collected. In the case of a plasma collection device, the membranes 145 have a pore size in the range of from about 0.1 microns to about 1.5 microns and preferably about 1.0 microns. Other blood fractions which are of interest and which may be separated by the fractionator 80 are protein-free filtrates and protein fractions, and membranes useful for these purposes would necessarily have pore sizes in the range of from about 50 Angstrom to about 0.05 microns.

The stack 140 is sealed in part and the plates thereof are accurately aligned by the tongue and groove mechanism previously described. More specifically, the tongue 219 on one of the external blood fraction collection plates 200 fits into the groove 158 of the adjacent one of the blood plates 150, the tongue 159 of which in turn fits into the groove 228 on the internal blood fraction collection plate 220. The tongue 229 on the internal blood fraction collection plate 220 fits into the groove 158 of the adjacent blood plate 150, the tongue 159 of which fits into the groove 215a on the other external blood fraction collection plate 200. These tongues and grooves are arranged to interfit with one another while accommodating therein the membranes 145 which, as illustrated in FIGS. 14–18, extend from edge to edge of the various plates. The usefulness of the tongue and groove construction is that the membranes 145 remain imperforate, which is critical to the design of the blood fractionator 80 and to the operation of the system 40, since membrane rupture or leakage can result in serious problems. Furthermore, an imperforate membrane effectively constructs blood flow channels without the need for gaskets or other fluid separating components. In any event, utmost care is taken to ensure the leak free nature of the membranes 145 and, to this end, the design of the device which provides an imperforate membrane 145 affords significant advantages.

Completing the fractionator 80 and coacting with the stack 40 is a blood fraction outlet manifold 240. Referring to FIGS. 4, 6, 7 and 17, the blood fraction outlet manifold 240 includes a body 241, preferably formed of plastic and of generally rectangular shape, which has parallel rectangular outer and inner faces 242 and 243. The outer face 242 is notched at the opposite ends thereof to define two reduced end portions 244, dimensioned to respectively fit snugly into the rectangular slots 206 of the external blood fraction collection plates 200. Integral with the outer face 242 centrally thereof and projecting outwardly therefrom perpendicular thereto is a tubular portion 245. Formed in the inner face 243 are three equidistantly spaced-apart bores, including a central bore 246 which extends all the way through the body 241 to the outer face 242 and communicates with the tubular portion 245 coaxially therewith, and two end bores 247 which extend into the end portions 244. Extending into the body 241 from one end thereof and providing communication among the bores 246 and 247 is a transverse channel 248, the open end of which is closed by a plug 249.

In assembly of the stack 140, the blood fraction outlet manifold 240 fits snugly into the notches 156 of the blood plates 150 and the notch 226 of the internal blood fraction collection plate 220, with the reduced end portions 244 of the body 241 respectively received snugly in the rectangular slots 206 of the external blood fraction collection plates 200 for trapping the blood fraction outlet manifold 240 in place. When thus assembled, the center bore 246 is disposed in alignment and fluid communication with the blood fraction outlet bore 238 of the internal plasma plate 220, while the end bores 247 are respectively disposed in alignment and fluid communication with the blood fraction outlet bores 218 of the external blood fraction collection plates 200, as is best illustrated in FIG. 17. When the parts have been thus assembled, the stack 140 is placed in a mold and plastic is injected around the entire periphery thereof, so as to cover the peripheral surfaces of the plates 150, 200 and 220 and overlap the outer surfaces 202 of the external blood fraction collection plates 200, filling the grooves 209 therein to define a plastic clamping ring 209a (see FIGS. 14, 16 and 17). The clamping ring 209a is held in place by the grooves 209 and, when the material of the clamping ring 209a cools it shrinks and holds the stack 140 in compression.

Referring to FIG. 14, it can be seen that when the stack 140 is assembled in the manner described above, the two blood plates 150 cooperate with the adjacent membranes 145 to form two separate blood flow passages 250 and 255 which extend longitudinally through the fractionator 80 substantially parallel to each other. More specifically, each of these blood flow passages 250 and 255 is defined by the blood flow channels 160 of the associated blood plate 150 and the associated inlet tube 162 and outlet tube 166. It can be seen that each of these blood flow passages 250 and 255 comprises a pair of parallel flow channels defined by the blood flow channels 160 of the associated blood plate 150. This design affords significant advantages, since it allows the blood flow passages 250 and 255 to be connected in series externally of the fractionator 80, as was described above in connection with the system 40.

This design which permits the blood to flow through the fractionator 80 twice through separate paths connected in series affords a number of significant advantages over the prior device disclosed in the copending application Ser. No. 523,007, which split the incoming blood stream among four parallel blood flow channels. It is known that at a given shear to pressure ratio, filtration rate is a function of blood flow. The higher the blood flow, the higher the filtration rate. The dual serial-connected paths through the fractionator 80 result in a flow rate twice that of the previous parallel-path design, for a given flow rate from the donor. Because the filtration rate is higher, a shorter flow path can be utilized without decreasing the filtration fraction obtained. Thus, in a constructional model of the present invention, the transfer portions 180 of the blood plates 150 and the collection portions 211 and 231 of the blood fraction collection plates 200 and 220 have a length of only 1.5 inches, as compared to the length of about 2.6 inches in the fractionator of the copending application Ser. No. 523,007.

In addition to significantly enhancing the compactness of the device, this shorter flow path serves to directly enhance filtration rate. It has been found that the filtration rate decrease over time with a 1.5 inch channel length is no greater than that with a 2.6 inch channel length. A decrease with time is usually greater when total surface area is reduced. The filtration rate is a function of the ratio of shear to pressure times viscosity. The higher the ratio the greater the filtration rate. This ratio can be shown to be a function of the ratio of blood channel height to blood channel length times viscosity. Thus, shortening the blood flow channel length will increase the shear to pressure times viscosity ratio, and thereby increase filtration rate. Also, flow resistance in rectangular flow channels is a linear function of channel length. Thus, the pressure drop in plates having a transfer portion 1.5 inches long is about one-half that of that plates with transfer portions 2.6 inches long. Pressure drop is also a linear function of flow. Consequently, reduction in the length of the transfer and collection portions of the plates by about one-half permits approximate doubling of the flow rate with no change in pressure. Finally, the reduction in size of the transfer and collection portions of the plates results in proportional reduction in the membrane area.

As indicated above, while in the preferred embodiment, the stack 140 has been illustrated as being comprised of five plates and four membranes, it will be appreciated that different numbers of plates could be utilized, which was also true of the fractionator device disclosed in the aforementioned copending application Ser. No. 523,007. However, in that prior device, the addition of plates and membrane layers had a relatively small effect, since with each additional blood flow channel added in parallel, there was a proportionate decrease in flow rate. In the fractionator 80 of the present invention, however, the addition of plates and membrane layers has a relatively large effect, since additional filtration channels are added with no significant decrease in flow rate.

In summary, the design of the fractionator 80 results in a device which is more compact than the device of the copending application Ser. No. 523,007, and yet which has been found to produce a significantly increased filtration rate, resulting in a significant increase in blood fraction filtered.

Figure 23:
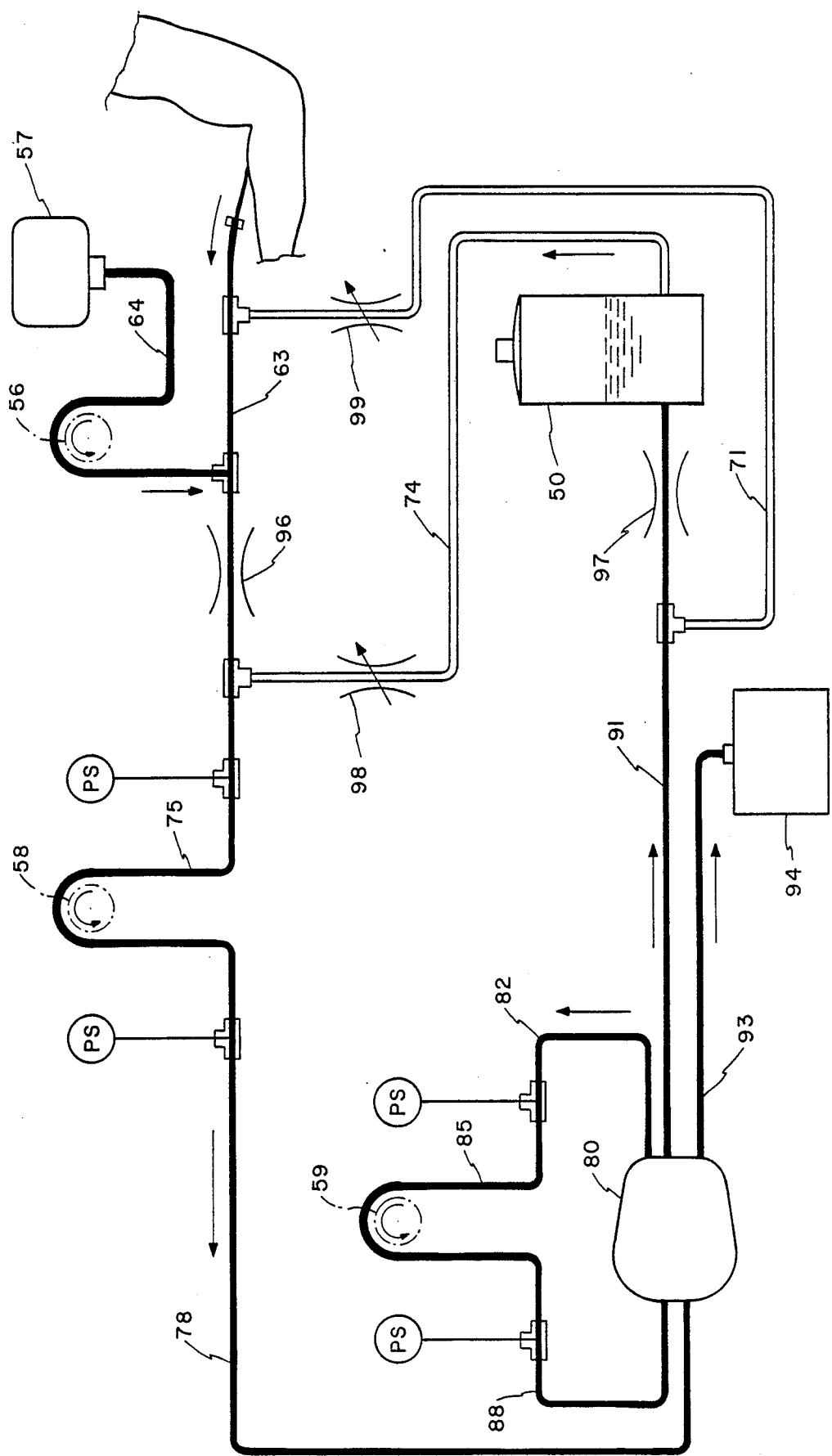
FIG. 23 is a diagrammatic view of the fluid transport portions of the system of FIG. 1, illustrating the fluid flow path when the valves are configured for a first pass through the system.
Figure 24:
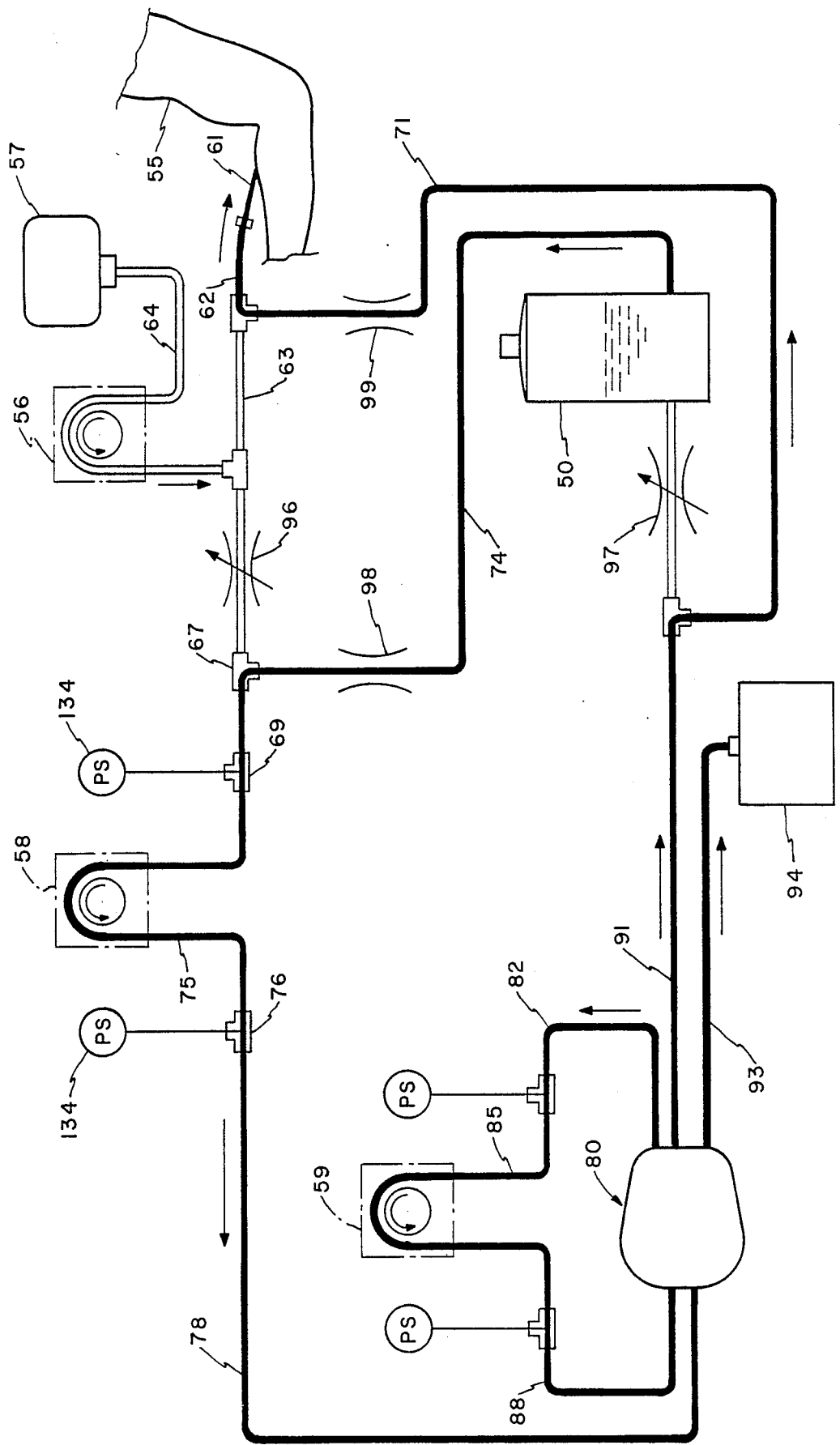
FIG. 24 is a view similar to FIG. 23, illustrating the fluid flow path when the valves are configured for a second pass through the system.

Referring now also to FIGS. 23 and 24, the general operation of the system 40 will be described. The use of the reservoir 50 permits a two-pass operation of the system 40, the first pass being illustrated in FIG. 23 and the second pass being illustrated in FIG. 24. More specifically, in the first pass the blood flows from the donor 55 through the fractionator 80 and to the reservoir 50, as indicated by the darkened portion of the tubing in FIG. 23. In second pass, the blood flows from the reservoir 50 through the fractionator 80 a second time and then back to the donor, as indicated by the darkened portion of the tubing in FIG. 24. The system 40 is designed to continuously recycle between the first and second passes until the predetermined amount of plasma has been collected. It can be seen that this two-pass operation has the advantages that the blood is passed two times through the fractionator 80 before it is returned to the donor 55, blood is continuously flowing in the needle 61 and, since the blood is alternately flowing in opposite directions therethrough, the needle 61 may be a single lumen needle.

Furthermore, it is significant that the unique design of the fractionator 80 with two separate blood flow passages 250 and 255 therethrough (see FIG. 14) connected in series externally of the fractionator 80 by the tubes 82, 85 and 88, means that during each pass of the system 40 the blood flows through both of the blood flow passages 250 and 255 in series, with the attendant advantages discussed above. During both of the first and second passes, plasma is continually being separated and fed to the plasma bag 94.

More particularly, during the first pass, it can be seen that blood flows from the donor 55 through the needle 61 to the blood pump 58, which pumps it to the first inlet 79 of the fractionator 80 and through the first blood flow passage 250. The blood is then pumped by the blood pump 59 from the outlet 81 of the blood flow passage 250 to the second inlet 89 of the fractionator 80, whence it flows through the second blood flow passage 255 to the reservoir 50. At the same time, anticoagulant is being pumped from the citrate bag 57 by the anticoagulant pump 56 into the blood flowing from the donor 55 at the mixing chamber 63. During this first pass, the valves 96 and 97 are open, while the valves 98 and 99 are closed to prevent blood from flowing from the reservoir 50 and to prevent blood flow directly from the donor 55 to the reservoir 50 without passing through the fractionator 80.

Referring to FIG. 24, during the second pass the condition is reversed, with the valves 96 and 97 being closed and the valves 98 and 99 being open, and the anticoagulant pump 56 is turned off. Thus, blood is prevented from flowing from the donor 55 or into the reservoir 50. Rather, blood flows from the reservoir 50 and is pumped by the blood pump 58 through the blood flow passage 250 of the fractionator 80, then is pumped by the blood pump 59 through the second blood flow passages 255 of the fractionator 80 and thence back through the needle 61 to the donor 55.

As was explained in greater detail in the aforementioned U.S. copending patent application Ser. No. 809,923, plasma volume is a physiological constant in vertebrates and approximates 5% of body weight, or 22.7 ml per pound. Plasma volume averages 62.5% of blood volume. If 18% of plasma volume is extracted, blood volume will decrease 11.3%. This blood volume decrease is less than that experienced by a 110 pound blood or plasma donor with a low hematocrit under current practices.

Ideally, volume of blood or plasma donated would be determined by the donor's size. Logistically this is impractical for manual plasmapheresis systems since the anticoagulant value and bag size would have to be individualized for each donor. As a consequence, manual plasmapheresis tends to withdraw proportionately large amounts of plasma from small donors and proportionately small amounts from large donors.

The present invention solves this problem by withdrawing the same proportion of available plasma from donors regardless of body size variations. This is achieved by utilization of automation and, in particular, microprocessor control of the system 40. Referring also to FIGS. 1 and 19, when the operator keys in the donor's weight and hematocrit values and, as will be explained in greater detail below, the system calculates the donor's plasma volume and volume of plasma to collect. Volume is estimated by continuous monitoring of the plasma weight collected in the plasma bag 94, as determined by the scale 95. The scale 95 is automatically set to zero at startup and weighs within +/−1 gram.

Pump calibration also depends upon the output of the electronic scale 95. The weight of fluid pumped within a fixed time integral at a known rpm is converted to volume per revolution. Blood flow is preset initially at 60 ml per minute but citrate flow depends upon plasma flow. Plasma flow, in turn, depends upon blood flow and hematocrit. The microprocessor 41 calculates the rpm for the blood pump 58 from the calibration values. The rpm for the citrate pump 56 is calculated from the calibration values, the blood flow and the hematocrit. Since coagulation factors are restricted to plasma, the anticoagulant/plasma concentration ratio is constant in all donors. This should be contrasted with manual techniques in which the anticoagulant volume is based upon blood, not plasma volume. In manual systems, there may be either an excess or a deficiency of anticoagulant, depending upon the hematocrit value.

If either blood pump 58 or 59 is slowed down by changes in pressure, all pumps slow proportionately and the ratio of citrate to plasma flow remains constant. The concentration of citrate used is low enough that systemic citrate levels are unlikely to reach toxic concentrations. Since citrate is metabolized rapidly as a normal metabolite, systemic anticoagulation cannot occur as is the case for anticoagulants such as heparin. The citrate and blood pumps are "all or none", i.e., they either pump the preselected amount or they pump nothing. This feature prevents undetected slowing down of one pump relative to the other. The blood pump 58 pumps faster than the citrate pump 56, so that citrate always flows toward the fractionator 80, and not toward the donor 55.

The input pressure of a pump is subatmospheric and its value depends upon inflow resistance and pump speed. The input pressure sensor monitors this pressure continuously. If the pressure falls below preset limits and pump speed has not changed, there must have been an increase of input resistance. The usual cause is inadequate blood flow from the vein. This, in turn, may be caused by kinked tubing, a poorly placed needle, or a blood clot in the input line. Conversely, a sudden rise of input pressure towards atmospheric pressure will occur if inflow resistance decreases. This almost always indicates a break in the input line with air influx. The output pressure of blood pump 58 is displayed on the pressure gauge 136. The output pressure of pump 59 is monitored, but is not displayed. The pressure of pump 58 always exceeds that of pump 59 and therefore reflects overall filtration pressure.

The major component of flow resistance is the fractionator 80, and this pressure approximates the separator transmembrane ("TM") pressure. This rise in the TM pressure for the blood pump 58 signifies increased resistance downstream from the blood pump 58. This may occur in the fractionator 80 or the return blood circuit. A slight rise during the procedure is normal and represents gradual membrane pore size reduction by protein deposition. A sudden fall in TM pressure is when a break occurs in the return circuit, such as line disconnection, dislodged needle or air influx.

During a plasmapheresis session, the system 40 continuously monitors pressure, flows, volume of plasma collected, and volume of citrate infused and collected. Blood flow initially begins at 60 ml/min. but may be increased to a maximum of 100 ml/min. or decreased, depending upon output (TM) pressures. This assures a maximum filtration rate in a given donor. When the calculated 18% of circulating plasma volume has been obtained, the system 40 shuts down automatically and prints out the results of the session. An automatic rinse cycle is provided to return the small amount of blood in the system to the donor 55.

It will be appreciated that the microprocessor 41 operates under stored program control, the operation of the program being illustrated in the flow diagram of FIGS. 32A–32G. The program is menu-driven, with the menu messages appearing on the display screen 42. The various display messages which appear during the operation of the program, the possible user replies and the response of the system 40 to these replies are all set forth in Table I at the end of the specification. Referring now to the flow diagram of FIGS. 32A–32G and the messages of Table I, the operation of the system 40 will be described.

START-UP MODULE

After the initial purge of air from the system and connection of the system to the donor, the system goes into the start-up loop. (FIG. 32A) The high and low level sensors 53 and 54 in the reservoir 50 and the bubble detector 62a are all connected in hardware to a single interrupt line. The sensors activate the interrupt when both are on or both are off. Both will be off when the level in the reservoir 50 is below the low level sensor 53. Both will be on when the level has reached the upper level sensor 54. The signals are ANDED with the signal from the bubble detector 62a so that a signal from the bubble detector 62a also will activate the interrupt hardware. Since a bubble in the system is of no consequence when fluid is flowing into the reservoir 50, the bubble interrupt is inactivated through software during this part of the cycle. On the other hand, if the bubble detector 62a is activated during the emptying cycle, the software will detect this and take the appropriate steps. Because the interrupt is not necessary during the initial startup during which the pumps go from zero to 40 ml/min blood flow, the interrupt is cleared at the beginning of the loop.

Sum Flow adds the flow rates of each pump as they are incremented during the startup procedure. Each time the loop is activated, the speeds of the three pumps are increased proportionately by Up Ramp until the blood flow has reached 40 ml/min. After each increment of flow the four pressures are checked by the Check Pressure subroutine (FIG. 32E) to be certain that they are not outside the limits set in the program. The reservoir sensors are read to detect fluid passage above the low level sensor. When this has happened, the interrupt is enabled in order to sense filling of the reservoir. Finally, the key pad is polled to see if STOP has been pressed by the user. The loop continues until the blood flow reaches 40 ml/min at which time it passes to the main program module shown in FIG. 32B.

MAIN PROGRAM MODULE

A counter is set to zero and the loop begins. The Check Pressure subroutine (FIG. 32E) is called. This routine continuously compares pressures with the preset limits and adjusts pump speeds accordingly. The Check Pressure routine is looped within the main loop until the pressures are within range. The counter then is incremented. When the count reaches 5, the screen is updated and the counter is reset to zero.

If the pressures are within range and the blood flow is less than 100 ml/min, the pump speeds are incremented proportionately at Up Ramp. If the pressures are not within range, there is no incrementation of pump speeds. The key pad is then polled to see if STOP has been pressed or if the user has requested a printout. Finally the volume of citrate given, as determined by the periodic summing of flows, is evaluated and if the amount given has exceeded 700 ml, a message is displayed on the screen. The message tells the user that he should check the citrate bag for possible replacement and also gives him the estimated amount of citrate needed to complete the procedure and the period of time over which this will occur. The last element in the loop is the Plasma Volume Collected which is evaluated to determine if the predetermined volume has been collected. When it has, the procedure is stopped.

Within the loop the submodule called Update Screen Display includes the module for evaluating total volumes collected during the procedure.

CHECK SIGNAL INTERRUPT

Figure 32A:
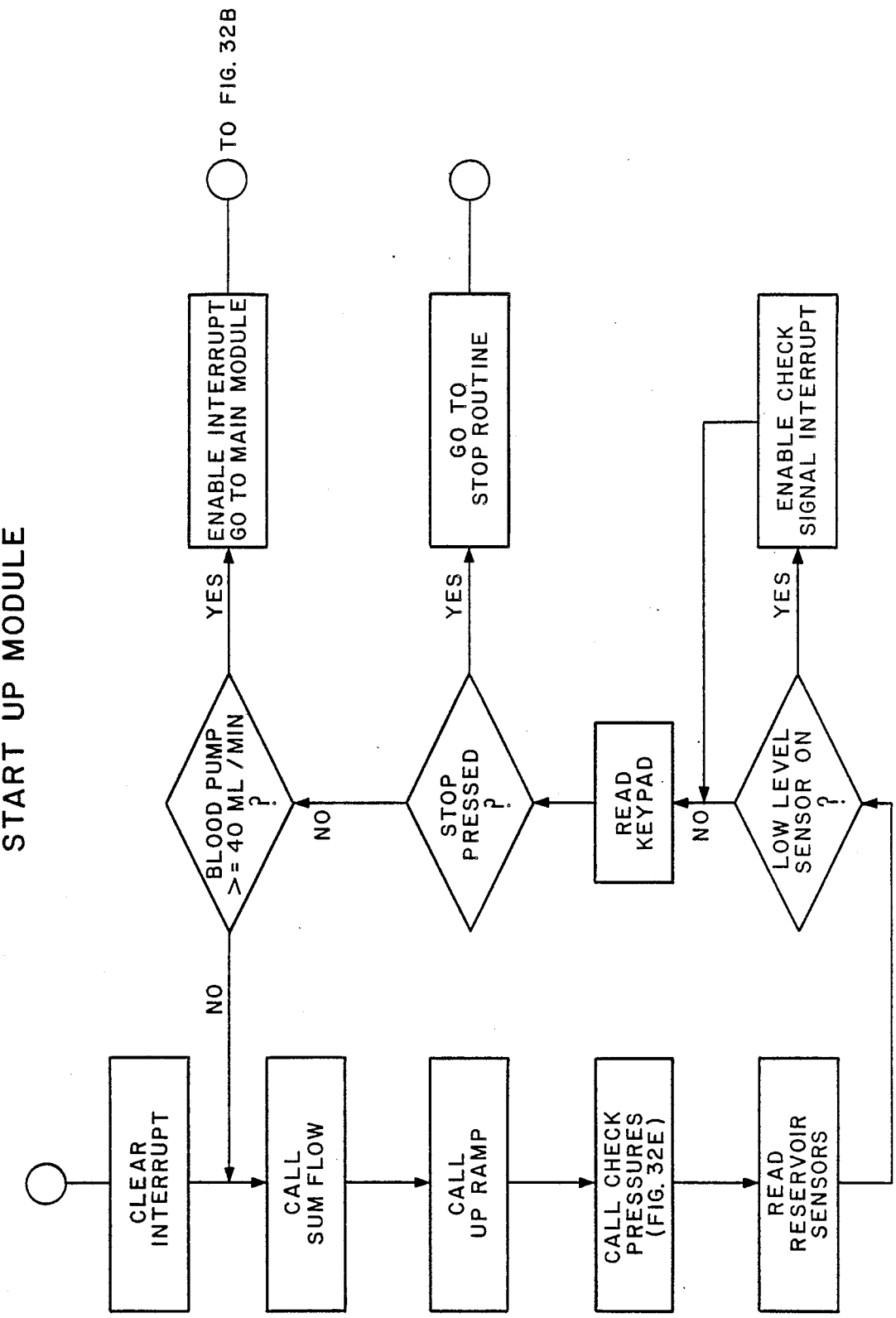
Figure 32B:
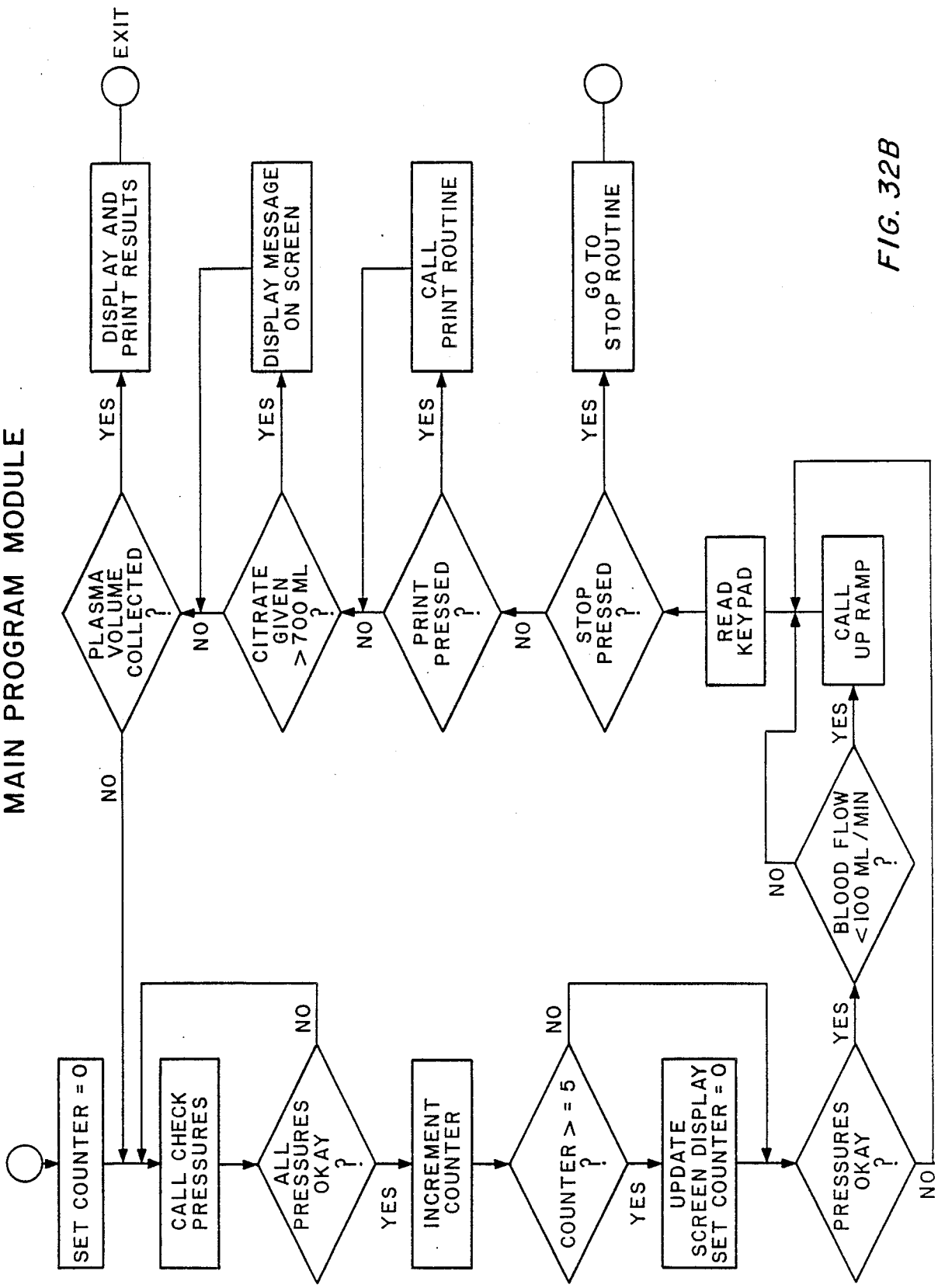
Figure 32C:
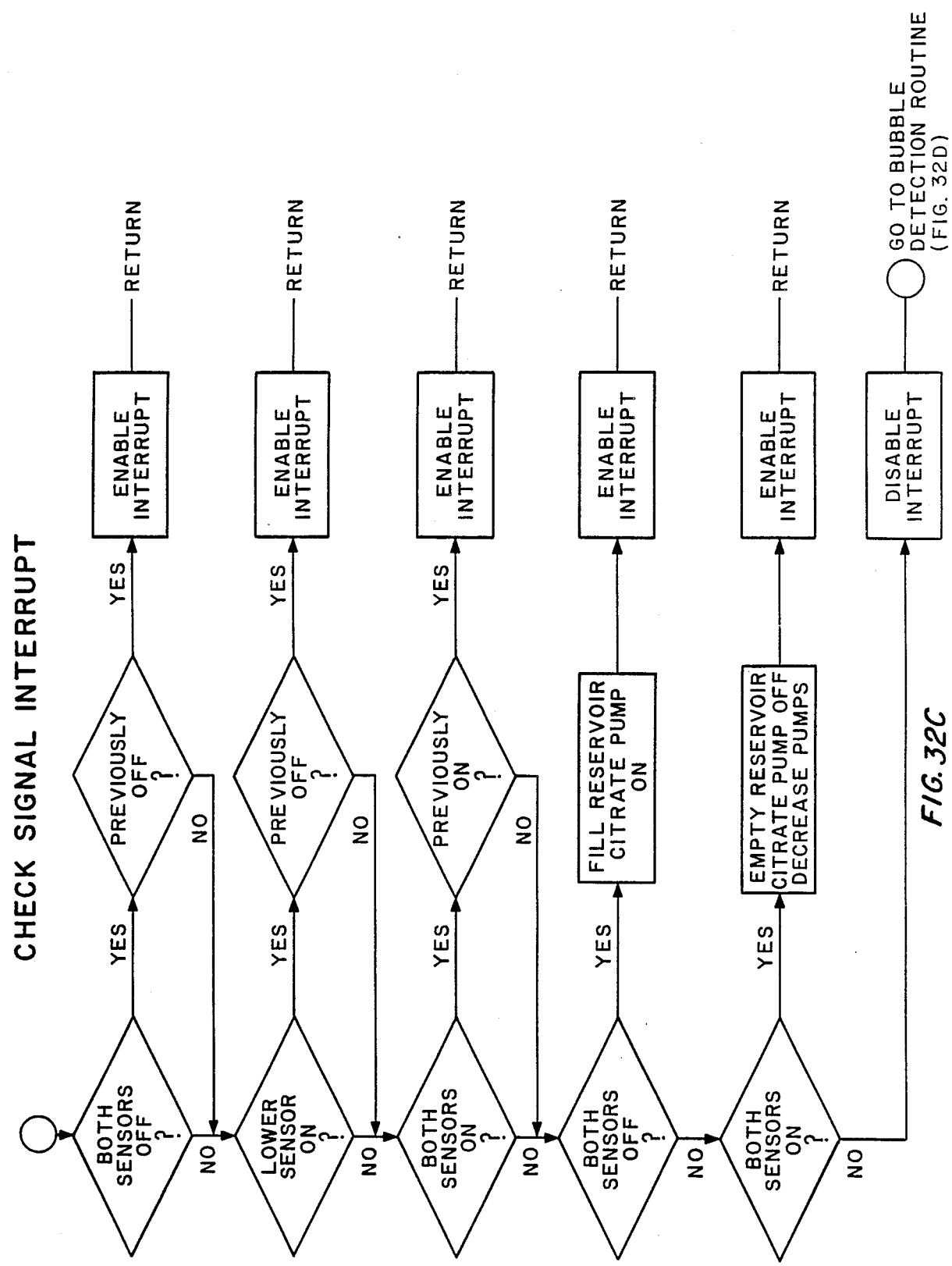

An interrupt is generated by the bubble detector 62a, when both sensors 53 and 54 are on, and when both sensors are off. The bubble detector is ignored in software if the reservoir 50 is filling. This loop, illustrated in FIG. 32C, shows the method by which the software handles the interrupt. When both sensors are off, the solenoids switch, the citrate pump 56 is turned on, and filling of the reservoir 50 begins. When both sensors are on, the solenoids switch, the reservoir is emptied and the citrate pump 56 is turned off. Because the blood in the reservoir 50 has a much higher concentration of red cells than the original donor blood, the flow resistance is increased during the emptying cycle of the reservoir. In order to prevent overpressurization of the system, the pump speeds are decreased proportionately at the onset of emptying of the reservoir.

Figure 32D:
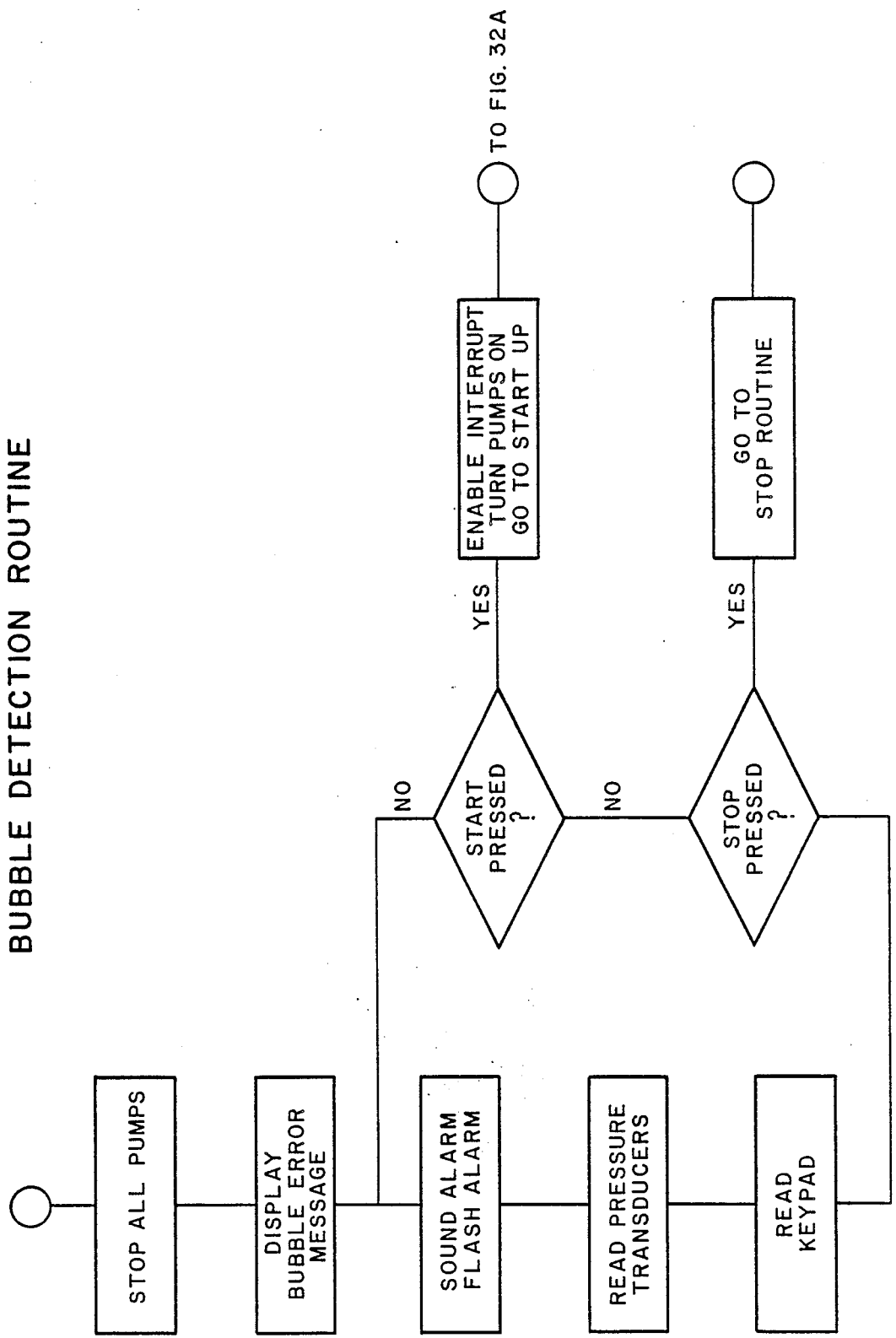
Figure 32E:
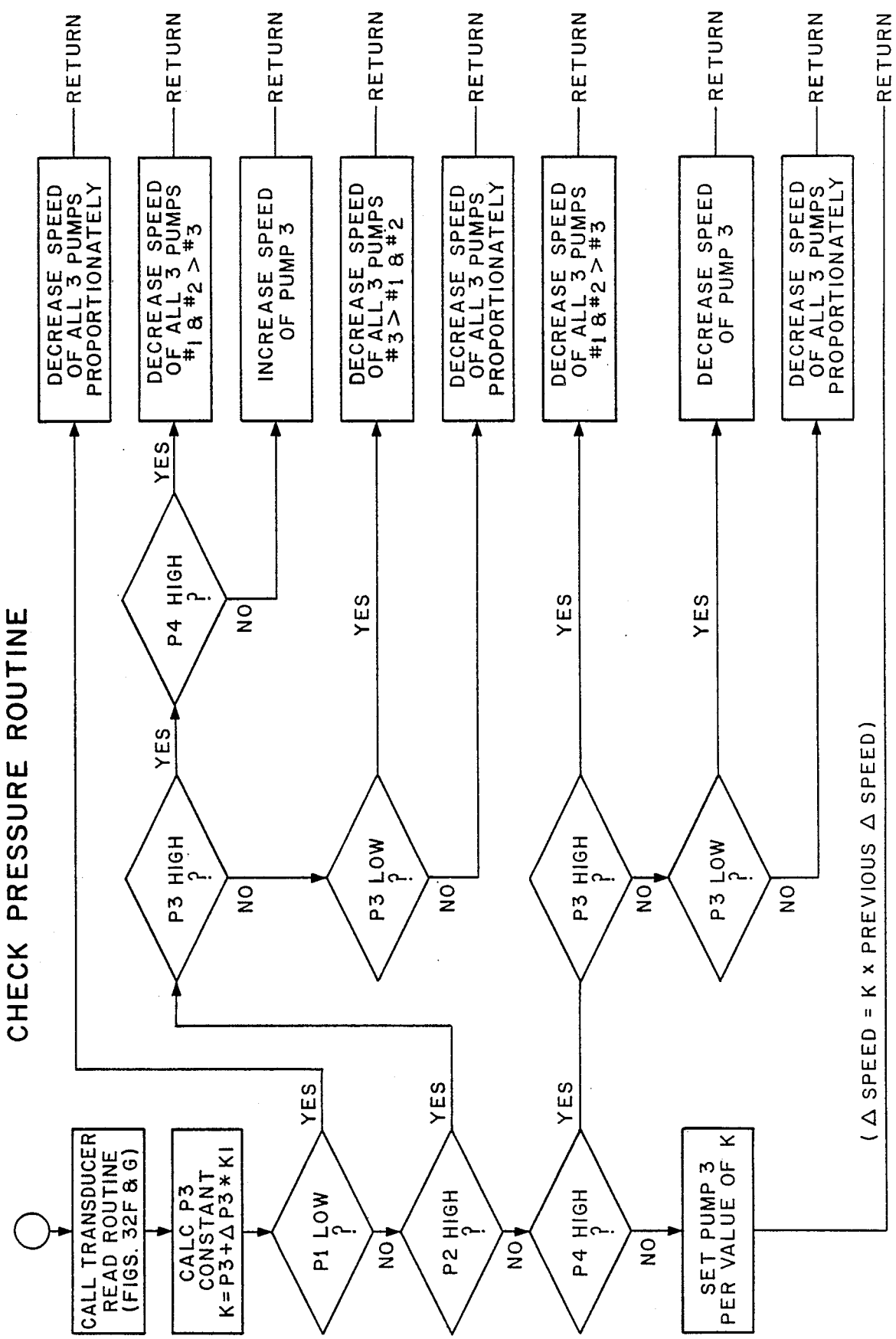

If an interrupt occurs during the emptying cycle of the reservoir, it falls through to the Bubble Routine shown in FIG. 32D.

BUBBLE DETECTION ROUTINE

This subroutine is entered from the Check Signal Interrupt and is discussed earlier. All pumps are stopped, the bubble error message is displayed, an alarm is sounded, and a red alarm is flashed. An internal loop continously reads the pressure trransducers and the key pad and the alarm continues until START or STOP are pressed. If STOP is pressed, the system goes the STOP routine where the user has the choice of permanently stopping or restarting the system. If START is pressed, the interrupt is re-enabled, the pumps are turned on, and the system goes to the Startup Module in FIG. 32A. This means that after correction of a bubble error, the pump flows start from zero and ramp up gradually to the appropriate flow rate as they do when the system is first started up.

CHECK PRESSURE ROUTINE

Pressure 3, which monitors the pressure between the output of the first stage of the fractionator 80 and the input of blood pump 59 (pump 3) is a closed volume. When pump 3 is running too slowly, pressure 3 rises. When pump 3 is running too rapidly, pressure 3 decreases. However, pressure 3 also reflects the difference between input to the first stage and the filtration rate of the fractionator 80. Should the filtration rate increase in the first stage, the input to pump 3 decreases so that pressure 3 falls. If on the other hand the filtration of the first stage decreases, the input to pump 3 increases and the pressure 3 rises. By modifying pump 3's flow rate so that pressure 3 oscillates around zero gage pressure, it is possible to maintain a balance between the two pumps 58 and 59.

The first item in the Check Pressure Routine is reading of the transducers by the Transfucer Read Routine shown in FIGS. 32F and G. A constant then is calculated for pump 3 which is defined as the current pressure plus the change in the pressure from the previous one multiplied by an empirically derived constant. The constant is weighted by the change in pressure 3 from the previous reading. According to the pressures obtained, the loop modifies pump speeds as necessary to correct the aberration.

TRANSDUCER READ ROUTINE

Each of the pressures are read sequentially and flags are set if any pressures are outside the preset limits.

Figure 25:
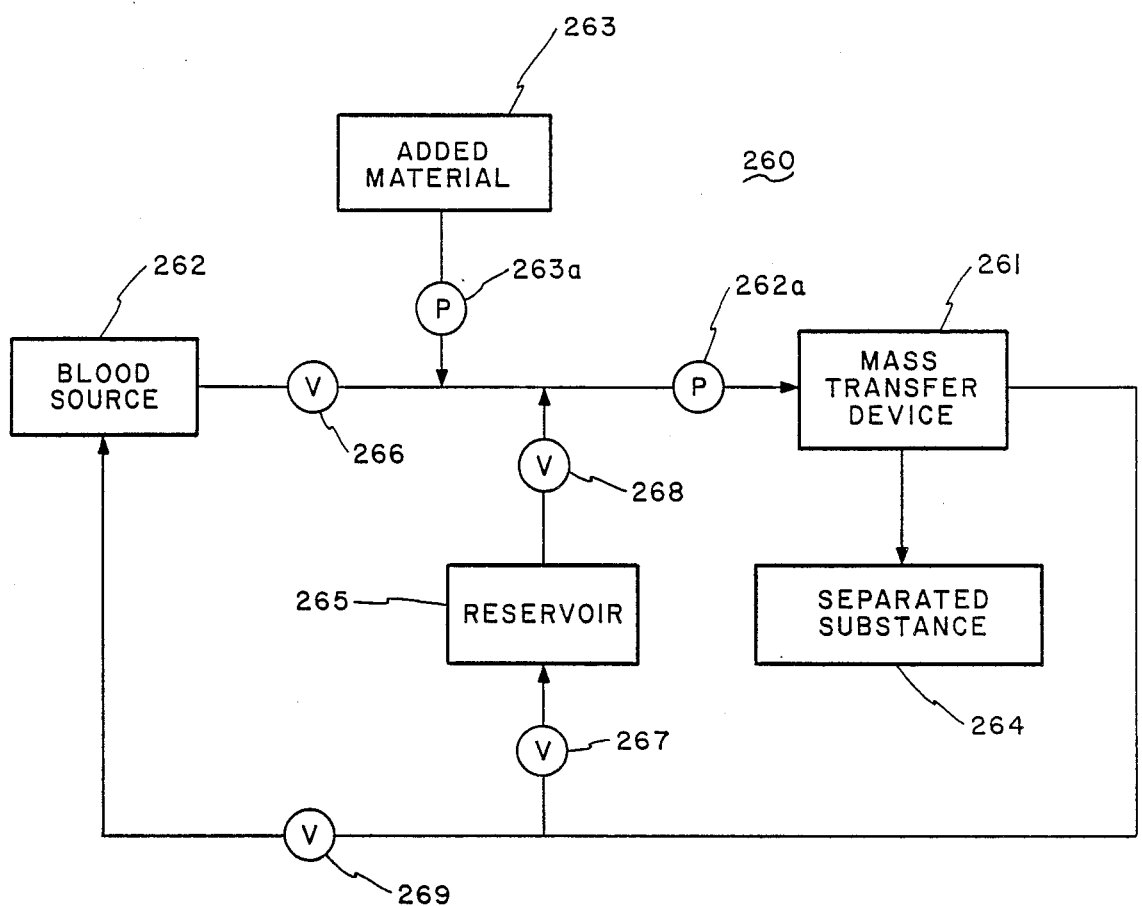
FIG. 25 is a block diagrammatic view of a system in accordance with another embodiment of the present invention.

While the principles of the invention have been described above in connection with a preferred embodiment relating to a plasmapheresis system, it will be appreciated that many of these principles are useful in other mass transfer applications. In FIG. 25 there is illustrated a generic mass transfer system, generally designated by the numeral 260, which incorporates the important features of the invention and has a number of specific applications. The system 260 includes a mass transfer device 261, a blood source 262 and a source 263 of material which is to be added to the blood. Coupled to the mass transfer device 261 is a separated substance collector 264. The system 260 is also provided with a reservoir 265, which serves the same function as the reservoir 50 in the blood fractionating system 40, described above. Blood from the source 262 is passed through a valve 266 and a suitable pump 262a to the mass transfer device 261. Added material from the source 263 is fed by a pump 263a into the blood flow at the input of the pump 262a. The output of the mass transfer device 261 is fed through a valve 267 to the reservoir 265 and through a valve 269 back to the blood source 262. Material from the reservoir 265 may be fed through a valve 268 to the input of the pump 262a.

In the system 40, described above, the mass transfer device 261 is the fractionator 80, the blood source is the donor 55 or other suitable source, the added material source 263 is the citrate bag 57, the separated substance collector 264 is the plasma bag 94, the reservoir 265 is the reservoir 50, the pumps 262a and 263a are the pumps 58 and 56, respectively, and the valves 266, 267, 268 and 269 are the valves 67, 97, 98, and 99, respectively.

Figure 26:
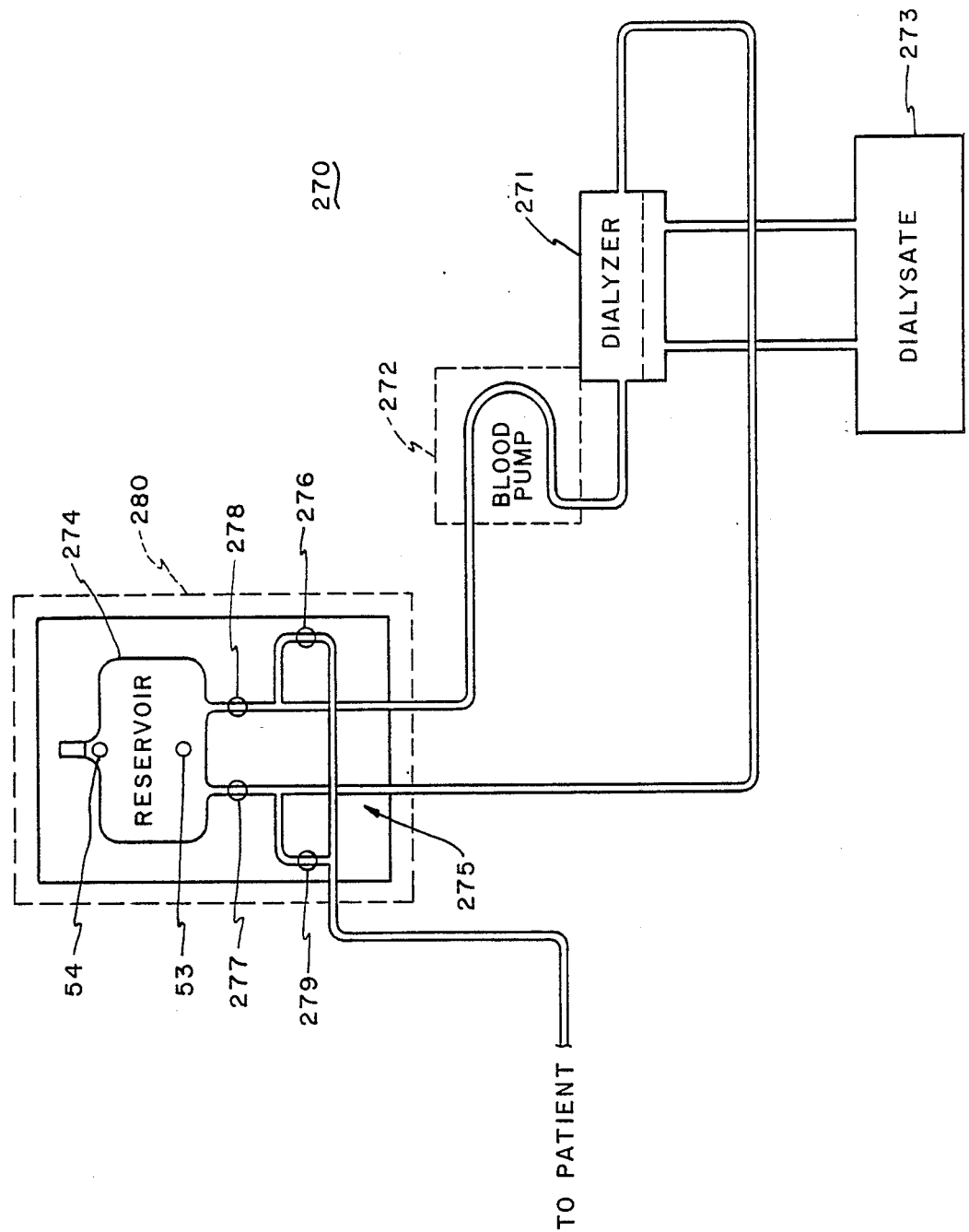
FIG. 26 is a diagrammatic view of the system of FIG. 25 configured for hemodialysis.
Figure 27:
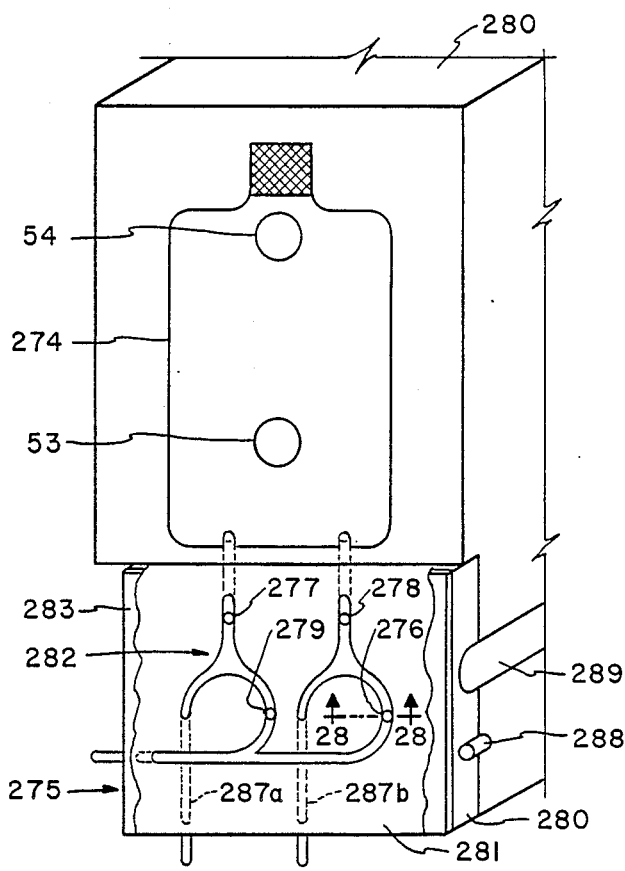
FIG. 27 is a fragmentary perspective view of a reservoir housing for the system of FIG. 26, utilizing a disposable manifold.

Referring to FIG. 26, there is illustrated a hemodialysis system 270 which is another species of the mass transfer system 260. In this case the mass transfer device is a dialyzer 271, and the blood source is a human patient to be dialyzed. Blood from the patient is fed to the dialyzer through a valve 276 and a blood pump 272, which respectively correspond to the valve 266 and the pump 262a in the system of FIG. 25. Impurities separated from the blood in the dialyzer 271 are collected in a dialysate collector 273, which corresponds to the separated substance collector 264. The output of the dialyzer 271 is fed to a reservoir 274 through a manifold 275. The manifold 275 includes the valve 276, and valves 277, 278 and 279, which respectively correspond to the valves 266-269 in the system of FIG. 25. The added material source 263 may be anticoagulant, some other desirable substance or nothing of the system of FIG. 25 is not used in the hemodialysis system 270.

In operation, in a first condition the valves 276 and 277 are open and the valves 278 and 279 are closed, and blood flows from the patient to the dialyzer 271 and thence to the reservoir 274. When the reservoir 274 is filled, as indicated by a level sensor 54, the condition of the valves switches to close the valves 276 and 277 and open the valves 278 and 279. In this condition blood flows from the reservoir 274 back through the dialyzer 271 and thence through the valve 279 back to the patient. When the reservoir 274 is nearly empty, as indicated by the level sensor 53, the condition of the valves again reverses and the cycle repeats.

The reservoir 274 and the manifold 275 may be disposable units and may be mounted in a reservoir housing 280. Referring to FIGS. 27 through 31, the manifold 275 may comprise channels and bores formed in a solid block 281 which is detachably mounted in the reservoir housing 280 beneath the reservoir 274. More specifically, the manifold includes a channel 282 formed in the upper or outer surface of the block 281, the channel 282 having a main line portion 284 adapted to communicate with the tubing to the patient, the main line portion 284 in turn communicating with two loop portions 285 and 285a (FIGS. 30 and 31), each of which defines approximately three-fourths of a circle. Respectively communicating with the loops 285 and 285a, approximately half way around the loops from their juncture with the main line portion 284 are upwardly extending stem portions 286 and 286a. At the distal ends of the mainline portion 284, the loop portions 285 and 285a and the stem portions 286 and 286a, the channel 282 communicates with bore portions 287 through 287d, respectively, which extend beneath the surface of the block 281 and exit at the side edges thereof for communication with associated tubing. A locating pin 288 may be provided for accurate positioning of the block 281 in the reservoir housing 280, and a latch 289 secures it in its mounted position.

When thus mounted in position, the bore 287 communicates with the tube to the patient, the bores 287a and 287b respectively communicate with the tubes leading to the outlet and the inlet of the dialyzer 271 and the bores 287c and 287d respectively communicate with tubes to the inlet and outlet of the reservoir 274. The cover plate 283 closes the open top of the channel 282.

The valves 276 through 279 are disposed in the reservoir housing 280 immediately behind the block 281 for cooperation with the manifold 275. More specifically, the valves 276 and 279 are respectively disposed in the loop portions 285a and 285 approximately midway between the main line portion 284 and the stem portions 286 and 286a, while the valves 277 and 278 are respectively disposed in the stem portions 286 and 286a. At the locations of the valves 276 through 279, the channel 282 opens all the way through to the bottom or back side of the block 281 to accommodate the valve mechanisms.

Figure 28:
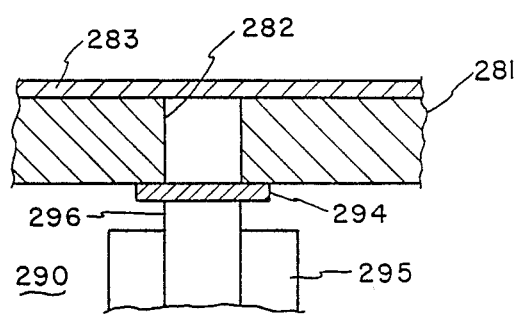
FIG. 28 is an enlarged fragmentary sectional view taken along the line 28—28 in FIG. 27, illustrating one of the valves cooperating with the disposable manifold of FIG. 27 and shown in the open condition.
Figure 29:
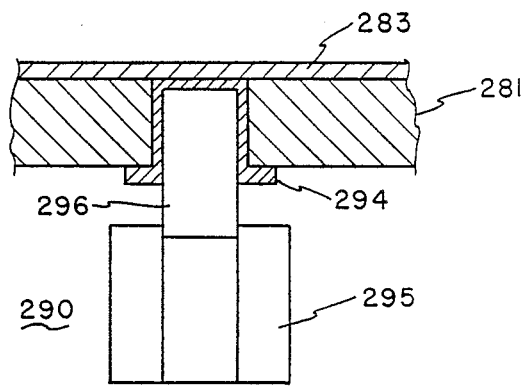
FIG. 29 is a view similar to FIG. 28, showing the valve in its closed condition.
Figure 30:
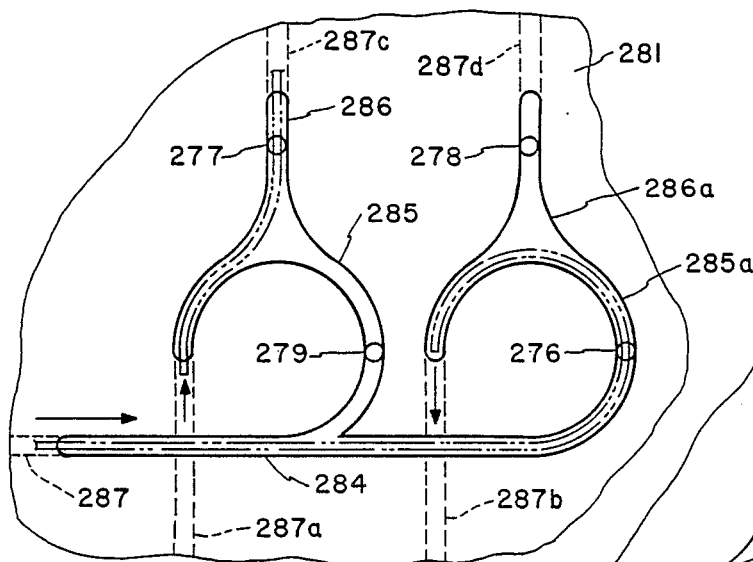
FIG. 30 is an enlarged fragmentary plan view of the disposable manifold of FIG. 27, with the cover plate removed and illustrating the fluid flow path when the valves are configured for a first pass through the system.
Figure 31:
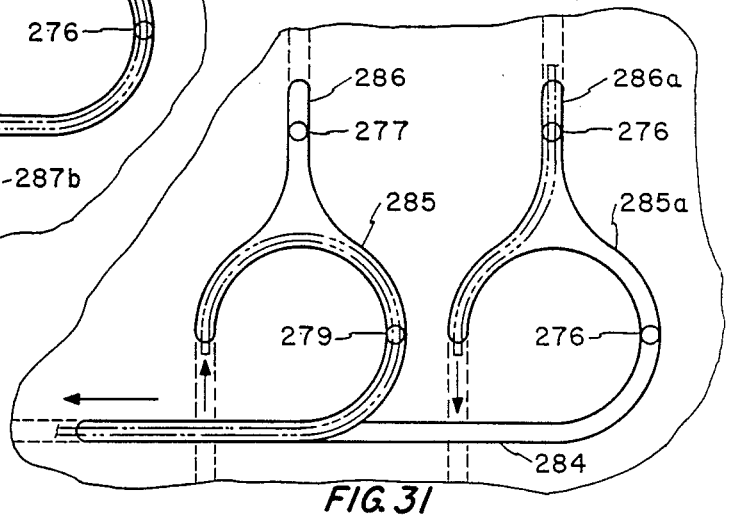
FIG. 31 is a view similar to FIG. 30, illustrating the fluid flow path when the valves are configured for a second pass to the system.

The valves 276 through 279 are substantially identical in construction and operation, wherefore only one will be described in detail. Referring to FIGS. 28 and 29, each of these valves is in the form of a valve 290, which includes a membrane 294 which covers the open portion of the channel 282 at the bottom or back side of the plate 281. Disposed immediately beneath the membrane 294 is solenoid 295, which has a plunger 296 disposed for contact with the membrane 294, and dimensioned to fit in the open portion of the channel 282. When the valve is opened, the plunger 296 is retracted, and the membrane 294 does not project into the channel 282, wherefore the channel 282 is unobstructed. When the valve 290 is closed, the solenoid 295 is actuated to drive the plunger 296 forwardly, stretching the membrane 294 into the channel 282 and against the cover plate 283, the parts being dimensioned so that the plunger 296 and the membrane 294 cooperate to completely close the channel 282 at the location of the valve 290 (see FIG. 29).

The system 260 of FIG. 25 may also be used for the washing of red blood cells, an operation which is performed both to prepare cells for freezing and to recover frozen cells, and also to remove plasma or cell debris in a blood bank or in a surgery. In operating the system 260 for preparing blood for freezing, the blood source 262 is a blood bag and the added material source 263 is a source of a suitable cryoprotective agent, such as glycerine. Initially, blood is run from the source 262 through the mass transfer device 261, which may be any suitable fractionator, while the cryoprotective agent is added. The cryoprotective agent displaces water from the blood cells, and the plasma and displaced water are removed in the fractionator. The blood from the fractionator passes to the reservoir 265. In the next pass of the cycle, blood from the reservoir again flows through the fractionator and then back to the source 262 for removing additional plasma. If desired, the cryoprotective agent may also be added during this second pass of the cycle for displacing additional water from the blood cells.

The system continues to cycle between its first and second passes until all of the water has been removed from the blood cells. This must be done gradually since, if the water is displaced from the cells faster than the cryoprotective agent is added, the cells will shrink, and if the cryoprotective agent is added too fast the cells will expand. The system 260 of the present invention, permits this to be done automatically under the control of the microprocessor which, for simplicity's sake, is not shown if FIG. 25. If the mass transfer device 261 is the fractionator 80, of the present invention, it will be appreciated that an additional pump may be used between the first and second stages of the fractionator 80, as illustrated in FIG. 1.

When the frozen blood is to be reconstituted, it is thawed and then run through the system 260, with saline being added from the added material source 263, to displace the cryoprotective agent in the blood cells. The displaced cryoprotective agent is removed by the mass transfer device 261. The system 260 is operated until all of the cryoprotective agent has been displaced, and there remains washed red blood cells.

It will be appreciated that the system 260 could also operate on whole blood, which has not been frozen, displacing water with saline to directly obtain washed red blood cells. Furthermore, while the system 260 includes the reservoir 265 for operation with two passes through the mass transfer device during each cycle, it will be appreciated that cell washing could also be performed without the reservoir 265 by continuous recirculation through the blood source 262 and the mass transfer device 261. This could be effected, for example, by simply closing the valves 267 and 268. This would still offer important advantages over prior batch-type cell washing techniques. Thus, it affords continuous flow which reduces handling, it is a closed system which facilitates maintenance of sterile conditions and it affords more efficient cell washing, since it ultimately mixes the saline and red blood cells as they are recirculated.

TABLE I

PROGRAM FOR CONSOLE WITH RESERVOIR

MESSAGE 1:

| WELCOME TO THE ARMOUR PLASMAPHERESIS SYSTEM PLEASE WAIT UNTIL THE SYSTEM IS TESTED INSTRUCTIONS WILL FOLLOW |
|---|

If transducers or scale are not functioning properly, the program goes to ERROR_MESSAGE 2A. .2C. Otherwise go to. MESSAGE 3.

MESSAGE 3:

| DIAGNOSTIC CHECKS WERE OKAY. FOR EMERGENCY START PRESS <<REDO>> TO SETUP SYSTEM PRESS <<ENTER>> |
|---|

If <<REDO>> is pressed, go to MESSAGE 4. If <<ENTER>> is pressed, go to MESSAGE 6.

MESSAGE 4:

| GO DIRECTLY TO START PLASMAPHERESIS?? PRESS <<YES>> OR <<NO>> |
|---|

If <<YES>> is pressed, go to MESSAGE 4. If <<NO>> is pressed, go to MESSAGE 3.

MESSAGE 5:

| DO YO WISH TO PURGE THE SYSTEM? PRESS <<YES>> OR <<NO>> |
|---|

If <<YES>> is pressed, go to MESSAGE 27. If <<NO>> is pressed, go to MESSAGE 29.

MESSAGE 6:

| THE DATE IS : THE TIME IS : CHANGE TIME OR DATE? PRESS <<YES>> OR <<NO>> |
|---|

If <<YES>> is pressed, go to MESSAGE 7. If <<NO>> is pressed, go to MESSAGE 9.

MESSAGE 7:

| ENTER THE DATE AS MM.DD.YY FOR EXAMPLE: 08.15.85 PRESS <<ENTER>> IF NO CHANGE ENTER DATE : |
|---|

MESSAGE 8:

| ENTER THE TIME AS HH.MM.SS0(AM) OR 1(PM) (12 HR TIME) FOR EXAMPLE: 11.12.000 PRESS <<ENTER>> IF NO CHANGE ENTER TIME : |
|---|

MESSAGE 9:

| DO YOU WISH TO CALIBRATE TRANSDUCERS? PRESS <<YES>> OR <<NO>> |
|---|

If <<YES>> is pressed, go to CAL_MESSAGE1. If <<NO>> is pressed, go to MESSAGE 10.

TABLE I-continued

TRANSDUCER MESSAGE:

> PRESSURE TRANSDUCERS MUST BE CALIBRATED
> LAST CALIBRATION WAS MORE THAN 1 WK AGO
> CALIBRATE INPUT LEVEL 1 FIRST
> PRESS <<ENTER>> TO CONTINUE

If transducers have not been calibrated recently, go to CAL_MESSAGE1.

MESSAGE 10:

> SCALE SHOULD BE CALIBRATED
> AT THE BEGINNING OF EACH DAY.
> DO YOU WISH TO CALIBRATE SCALE?
> PRESS <<YES>> OR <<NO>>

If <<YES>> is pressed, go to MESSAGE 11. If <<NO>> is pressed, go to MESSAGE 16.

MESSAGE 11:

> REMOVE ALL OBJECTS FROM SCALE
> INCLUDING BAG HOLDER CLAMP
>
> PRESS <<START>> WHEN READY

MESSAGE 12:

> THIS PROCEDURE MUST BE PERFORMED
> PLACE 2 KG WEIGHT IN CENTER OF SCALE.
>
> PRESS <<START>> WHEN READY

MESSAGE 13:

> REMOVE 2 KG WEIGHT FROM SCALE.
>
> PRESS <<START>> WHEN READY

MESSAGE 14:

> PLEASE VERIFY CALIBRATION.
> PLACE 2 KG WEIGHT IN CENTER OF SCALE.
>
> PRESS <<START>> WHEN READY

MESSAGE 15:

> THE MEASURED WEIGHT IS:     GRAMS.
> DIFFERENCE FROM 2 KG IS:     GRAMS.
> THE SCALE IS WITHIN TOLERANCE.
> PRESS <<START>> WHEN READY

If scale varies from standard more than 2 grams, go to SCALE_ERROR.

MESSAGE 16:

> PUMPS SHOULD BE CALIBRATED
> AT THE BEGINNING OF EACH DAY.
> DO YOU WISH TO CALIBRATE THEM?
> PRESS <<YES>> OR <<NO>>

If <<NO>> is pressed, go to MESSAGE 22. If <<YES>> is pressed, go to MESSAGE 17.

MESSAGE 17:

> REMOVE BAG HOLDER CLAMP FROM SCALE
> POSITION CONTAINER AND TUBES IN SCALE
> ADJUST PUMPS FOR PROPER OCCLUSION
> PRESS <<START>> WHEN READY

MESSAGE 18:

> CITRATE PUMP CALIBRATION IN PROGRESS
> NO OF GRAMS :
> NO OF SECONDS :
> PRESS <<STOP << TO HALT PROCESS

Screen is updated every 5 seconds.

MESSAGE 19:

> BLOOD PUMP #1 CALIBRATION IN PROGRESS
> NO OF GRAMS :
> NO OF SECONDS :
> PRESS <<STOP>> TO HALT PROCESS

Screen is updated every 5 seconds.

TABLE I-continued

MESSAGE 20:

> BLOOD PUMP #2 CALIBRATION IN PROGRESS
> NO OF GRAMS :
> NO OF SECONDS :
> PRESS <<STOP>> TO HALT PROCESS

Screen is updated every 5 second.

STOP_PUMP1:

> CITRATE PUMP CALIBRATION STOPPED
>
> PRESS <<REDO>> TO RESTART SETUP

<<REDO>> returns to MESSAGE 17.

STOP_PUMP2:

> BLOOD PUMP #1 CALIBRATION STOPPED !
>
> PRESS <<REDO>> TO RESTART SETUP

<<REDO>> returns to MESSAGE 17.

STOP_PUMP3:

> BLOOD PUMP #2 CALIBRATION STOPPED !
>
> PRESS <<REDO>> TO RESTART SETUP

<<REDO>> returns to MESSAGE 17.

MESSAGE 21:

> ALL PUMPS ARE CALIBRATED.
>
> PRESS <<REDO>> TO RESTART SETUP
> PRESS <<ENTER>> TO CONTINUE

<<REDO>> returns to MESSAGE 17.

MESSAGE 22:

> ENTER THE DONOR ID NUMBER :
> PRESS <<ENTER>> IF NO CHANGE

MESSAGE 23:

> ENTER DONOR SEX (1=FEMALE; 2=MALE):
> PRESS <<ENTER>> IF NO CHANGE

MESSAGE 24:

> ENTER DONOR HEMATOCRIT (PER CENT):
> PRESS <<ENTER>> IF NO CHANGE

If hematocrit is out of range,
go to HEMATOCRIT_ERROR1..3.

MESSAGE 25:

> ENTER DONOR WEIGHT IN LBS:
> PRESS <<ENTER>> IF NO CHANGE

If weight is out of range, go
to WEIGHT_ERROR1 OR WEIGHT_ERROR2.

MESSAGE 26:

> DONOR      IS
> BODY WEIGHT IS      POUNDS
> HEMATOCRIT IS       PER CENT
> CHANGE VALUES? <<YES>> OR <<NO>>

If <<YES>> is pressed, go to MESSAGE 22.

MESSAGE 27:

> INSTALL PLASMAPHERESIS DISPOSABLES
> PLACE BAG OF CITRATE SOLUTION ON HOLDER
> ASSIST AIR REMOVAL BY GENTLY TAPPING
> PRESS <<START>> TO BEGIN PURGE CYCLE

TABLE I-continued

WAIT MESSAGE:

> PLEASE WAIT FOR A FEW MOMENTS

MESSAGE 28:

> WHEN ALL AIR IS PURGED PRESS <<STOP>>

MESSAGE 29:

> YOU WILL NEED   PLASMA BAGS
> TOTAL VOLUME TO BE COLLECTED IS ML
> PLEASE PLACE REQUIRED BAGS IN SCALE
> PRESS <<START>> WHEN READY

MESSAGE 30:

> INSERT NEEDLE INTO DONOR'S VEIN.
> REMOVE CLAMP FROM PLASMA LINE
> WHEN BLOOD EXITS THE SEPARATOR.
> PRESS <<START>> WHEN READY

DISPLAY_MESSAGE:

> TOTAL RUN TIME ELAPSED =    MIN
> DILUTE PLASMA COLLECTED =   ML
> DONOR PLASMA COLLECTED =    ML
> TOTAL CITRATE RETURNED =    ML

Screen updated every 5-8 seconds.

STOP_MESSAGE:

> PROCEDURE HAS BEEN STOPPED.
> DO YOU WISH TO STOP THE PROCESS?
> PRESS <<YES>> OR <<NO>>

If <<YES>> is pressed, go to END_PROGRAM MESSAGE. If <<NO>> is pressed, restart system and update screen.

CITRATE_MESSAGE:

> ABOUT 700 ML OF CITRATE HAS BEEN PUMPED
> PLUS VOLUME USED FOR PURGING AIR
> MIN. TO END=    ;ML CITRATE TO END=
> CHECK CITRATE BAG-PRESS START WHEN READY

END-PROGRAM MESSAGE:

> PROCEDURE HAS BEEN STOPPED.
> ALL PATIENT DATA HAS BEEN ERASED.
> THE CONSOLE IS READY FOR A NEW PROCEDURE
> PRESS <<START>> WHEN READY

TRANSDUCER CALIBRATION MESSAGES

CAL_MESSAGE1:

> REMOVE CONNECTIONS TO INPUT LEVEL 1
> PRESS <<START>> WHEN READY

CAL_MESSAGE2:

> REMOVE CONNECTIONS TO OUTPUT LEVEL 1
> PRESS <<START>> WHEN READY

TABLE I-continued

CAL_MESSAGE3:

> REMOVE CONNECTIONS TO INPUT LEVEL 2
> PRESS <<START>> WHEN READY

CAL_MESSAGE4:

> REMOVE CONNECTIONS TO OUTPUT LEVEL 2
> PRESS <<START>> WHEN READY

CAL_MESSAGE5:

> ATTACH GAGE LINE TO LEVEL 1 INPUT
> ADJUST GAUGE TO READ ABOUT      MMHG
> ENTER EXACT READING ON GAGE:
> (message repeated for each transducer)
> (4 pressures used for each transducer)

ERROR MESSAGES

ERROR_MESSAGE 2A:

> LEVEL 1 TRANSDUCERS ARE NOT FUNCTIONING
> PLEASE CHECK TROUBLE SHOOTING MANUAL

ERROR_MESSAGE 2B:

> LEVEL 2 TRANSDUCERS ARE NOT FUNCTIONING
> PLEASE CHECK TROUBLE SHOOTING MANUAL

ERROR_MESSAGE 2C:

> THE SCALE IS NOT FUNCTIONING PROPERLY
> PLEASE CHECK TROUBLE SHOOTING MANUAL

FORMAT_ERROR:

> DATE FORMAT IS MM.DD.YY
> USE ZERO IF NO NUMBER.
> PLEASE REENTER DATE.
> PRESS <<START>> WHEN READY

CONTENT_ERROR:

> THIS IS YOUR DATE ENTRY:
> EITHER THE DAY OR MONTH IS WRONG.
> DATE FORMAT IS MM.DD.YY PLEASE REENTER
> PRESS <<START>> WHEN READY

TIME_FORMAT:

> TIME FORMAT IS HH.MM.SS0
> USE ZERO IS NO NUMBER.
> PLEASE REENTER TIME.
> PRESS <<START>> WHEN READY

TIME_CONTENT:

> THIS IS YOUR TIME ENTRY:
> HOUR, MINUTE, SECOND OR AM/PM IS WRONG.
> TIME FORMAT IS HH.MM.SS0 PLEASE REENTER
> PRESS <<START>> WHEN READY

TABLE I-continued

SCALE_ERROR:

> THE MEASURED WEIGHT IS:     GRAMS.
> DIFFERENCE FROM 2 KG IS:     GRAMS.
> OUT OF TOLERANCE - PLEASE RECALIBRATE
> PRESS <<START>> WHEN READY

SCALE_FAILURE:

> SCALE MALFUNCTION. PLEASE TURN OFF
> THE MACHINE AND REFER TO THE
> TROUBLESHOOTING GUIDE IN THE MANUAL.

If calibration fails 5 times, this message displays and program halts.

HEMATOCRIT_ERROR1:

> HEMATOCRIT ENTERED IS     PER CENT
> THE VALUE IS TOO LOW FOR A FEMALE
> IS THIS HEMATOCRIT CORRECT?
> PRESS <<YES>> OR <<NO>>

If <<YES>> is pressed, go to END_OF_DONOR. If <<NO>> is pressed, go to MESSAGE 24.

HEMATOCRIT_ERROR2:

> HEMATOCRIT ENTERED     IS PER CENT
> THE VALUE IS TOO LOW FOR A MALE
> IS THIS HEMATOCRIT CORRECT?
> PRESS <<YES>> OR <<NO>>

If <<YES>> is pressed, go to END_OF_DONOR. If <<NO>> is pressed, go to MESSAGE 24.

HEMATOCRIT_ERROR3:

> HEMATOCRIT ENTERED IS     PER CENT
> THE VALUE IS TOO HIGH FOR THIS PROCESS
> IS THIS HEMATOCRIT CORRECT?
> PRESS <<YES>> OR <<NO>>

If <<YES>> is pressed, go to END_OF_DONOR. If <<NO>> is pressed, go to MESSAGE 24.

WEIGHT_ERROR1:

> DONOR WEIGHT ENTERED IS     POUNDS.
> THE WEIGHT IS LESS THAN 110 POUNDS!
> IS THIS WEIGHT CORRECT?
> PRESS <<YES>> OR <<NO>>

If <<YES>> is pressed, go to END_OF_DONOR. If <<NO>> is pressed, go to MESSAGE 25.

WEIGHT_ERROR2:

> DONOR WEIGHT ENTERED IS     POUNDS.
> THE WEIGHT IS MORE THAN 300 POUNDS!
> IS THIS WEIGHT CORRECT?
> PRESS <<YES>> OR <<NO>>

If <<YES>> is pressed, go to END_OF_DONOR. If <<NO>> is pressed, go to MESSAGE 25.

END-OF-DONOR:

> SORRY. THIS DONOR IS UNACCEPTABLE.
>
> PRESS <<RESET>> TO RESET THE MACHINE

CAL_ERROR MESSAGE:

> YOU HAVE USED THE WRONG PRESSURE
> THE NUMBER ENTERED IS TOO LARGE
> PLEASE RESTART CALIBRATION PROCEDURE
> PRESS <<ENTER>> TO CONTINUE

PRESSURE_ERROR1:

> *INPUT PRESSURE LEVEL 1 TOO LOW*
> CHECK FOR OCCLUDED OR KINKED INPUT LINE
> CHECK NEEDLE FOR OCCLUSION.
> PRESS <<START>> WHEN CORRECTED

PRESSURE_ERROR2:

> *OUTPUT PRESSURE LEVEL 1 TOO HIGH*
> CHECK FOR OCCLUDED OR KINKED RETURN LINE
> CHECK SEPARATOR AND BUBBLE DETECTOR.
> PRESS <<START>> WHEN CORRECTED

TABLE I-continued

PRESSURE_ERROR3:

```
*OUTPUT PRESSURE LEVEL 2 TOO HIGH*
CHECK FOR OCCLUDED OR KINKED RETURN LINE
   CHECK SEPARATOR AND BUBBLE DETECTOR.
      PRESS <<START>> WHEN CORRECTED
```

BUBBLE_ERROR:

```
    AIR DETECTED IN RETURN LINE
 CHECK CONNECTIONS BEFORE CITRATE PUMP
 AND AFTER SEPARATOR. PRESS <<START>>
   WHEN CORRECTED OR <<STOP>> TO QUIT
```

PRINTER MESSAGES

PUMP CAL PRINT:

```
    CITRATE PUMP =    ML/REV.
    BLOOD PUMP #1 =   ML/REV.
    BLOOD PUMP #2 =   ML/REV.
```

PRINT_START MESSAGE:

```
BEGIN PROCEDURE
TIME :
DATE :
DONOR :
DONOR WEIGHT       POUNDS
MALE(female)
HEMATOCRIT =
BLOOD FLOW IS      ML/MIN
CITRATE FLOW IS    ML/MIN
DILUTE PLASMA
TO BE COLLECTED IS    ML
PLASMA VOLUME
TO BE COLLECTED IS    ML
```

PRINT MESSAGE:

```
TIME :
DATE :
DONOR :
DONOR WEIGHT       POUNDS
MALE(female)
HEMATOCRIT =
VOLUME COLLECTED:
PLASMA =       ML.
DILUTE PL =    ML.
CITRATE RETURN =    ML.
```

PRINT_END MESSAGE:

```
PROCEDURE ENDED
TOTAL TIME =    MINUTES
SETUP TIME =    MINUTES
RUN TIME =      MINUTES
TIME :
DATE :
DONOR :
DONOR WEIGHT       POUNDS
MALE(female)
HEMATOCRIT =
VOLUME COLLECTED:
PLASMA =       ML.
DILUTE PL =    ML.
CITRATE RETURN =    ML.
```

I claim:

1. A device for continuously producing a blood fraction, comprising: a stack of alternating plates and semipermeable membranes, said membranes being selectively permeable to the blood fraction, said plates including at least two blood flow channels and at least two collection channels therein, said blood flow channels respectively facing said collection channels and being respectively separated therefrom by said semipermeable membranes, two blood inlets and two blood outlets respectively communicating with said blood flow channels, said plates including wall means preventing fluid communication between said two blood flow channels internally of the device, each blood flow channel having a transfer portion extending longitudinally thereof, each collection channel having a collection portion disposed substantially in registry with said transfer portion of said facing blood flow channel for receiving the blood fraction passing through the associated one of said membranes, and a fraction outlet for conducting the blood fraction from each of said collection channels, whereby the blood fraction continuously transfers from blood passing through said transfer portions of said blood flow channels through said membranes into said adjacent collection channels and to said fraction outlet.

2. The device of claim 1, wherein said blood flow channels are arranged substantially parallel to each other.

3. The device of claim 1, wherein said stack includes two pairs of said blood flow channels with the channels of each pair connected in parallel and communicating with one of said blood inlets and one of said blood outlets, said wall means preventing fluid communication of either of the blood flow channels of one pair with either of the blood flow channels of the other pair internally of the device.

4. The device of claim 3, wherein said stack includes five of said plates alternating with four of said semipermeable membranes.

5. The device of claim 1, wherein each of said blood flow channels includes a distribution portion comprising a multiple bifurcated manifold wherein the depth of said manifold increases from said transfer portion to said blood inlet.

6. The device of claim 5, wherein each of said blood flow channels includes a combining portion for conducting blood from said transfer portion to said blood outlet, each of said collection channels including a combining portion disposed substantially in registry with said combining portion of said facing blood flow channel for conducting the blood fraction from said collection portion to said fraction outlet, each of said combining portions comprising a multiple bifurcated manifold.

7. The device of claim 5, wherein each of said collection channels includes a multiple bifurcated manifold communicating with said collection portion and disposed substantially in registry with said distribution portion manifold of said facing blood flow channel.

8. The device of claim 1, and further comprising two inlet tubes and two outlet tubes fixedly secured to said stack and projecting longitudinally outwardly therefrom and respectively communicating with said blood inlets and blood outlets.

9. The device of claim 1, wherein said plates respectively have aligned openings therein at one end thereof, and further comprising a blood fraction manifold member receivable in said aligned openings and communicating with each of said collection channels, said fraction outlet being formed on said manifold member.

10. A system for continuously fractionating blood in situ, comprising: fractionating means having first and second independent passages therethrough for continuously producing a blood fraction, each of said passages having a blood inlet and a blood outlet and a blood flow channel providing communication therebetween, said fractionating means having a blood fraction collection channel and a blood fraction outlet communicating therewith, said fractionating means including wall means preventing fluid communication between said blood flow channels internally of said fractionating means, conduit means coupling the blood source to the inlet of said first blood flow channel and to the outlet of said second blood flow channel and coupling the outlet of said first blood flow channel to the inlet of said second blood flow channel for establishing a closed path, pump means for moving blood along said closed path from a blood source through said first and second blood flow channels and back to the blood source for continuously producing a blood fraction in said blood fraction collection channel, and means coupled to said blood fraction outlet for collecting the blood fraction produced.

11. The system of claim 10, and further comprising means for controlling the flow of blood along said closed path.

12. The system of claim 11, wherein said flow controlling means includes pressure sensing means for producing pressure signals, and means responsive to said pressure signals for controlling the operation of said pump means.

13. The system of claim 10, and further comprising means for adding anticoagulant to the blood flowing from the blood source.

14. The system of claim 10, wherein said pump means includes a first pump disposed between the blood source and the inlet of said blood flow channel of said first passage, and a second pump disclosed between the outlet of said blood flow channel of said first passage and the inlet of said blood flow channel of said second passage.

15. A system for continuously separating a blood substance from a blood source in situ, comprising: separating means for continuously separating a blood substance from blood flowing therethrough, reservoir means, conduit means defining a closed path among the blood source and said separating means and said reservoir means, pump means for moving blood along said closed path, anticoagulant means for introducing anticoagulant to said conduit means closely adjacent to the blood source to provide means to prevent the system from containing stagnant blood which has not been anticoagulated, valve means coupled in said conduit means and operable between first and second conditions, said valve means in the first condition thereof permitting blood flow from the blood source through said separating means and into said reservoir means while preventing blood flow from said reservoir means and to the blood source, said valve means in the second condition thereof permitting blood flow from said reservoir means through said separating means and to the blood source while preventing blood flow from the blood source through said separating means, and control means coupled to said valve means for effecting operation thereof between the first and second conditions thereof, said pump means being operable when said valve means is in the first condition thereof for moving blood from the blood source through said separating means and to said reservoir means for continuously separating the blood substance, said pump means being operable when said valve means is in the second condition thereof for moving blood from said reservoir means through said separating means and to the blood source for continuously separating the blood substance.

16. The system of claim 15, and further comprising means for sensing the amount of blood in the reservoir.

17. The system of claim 15, wherein said sensing means includes means for producing signals indicative of the blood level in said reservoir means, said control means being coupled to said sensing means and being responsive to said signals for operating said valve means to the second condition thereof when said reservoir means is substantially full and for operating said valve means to the first condition thereof when said reservoir means is substantially empty.

18. A system for continuously fractionating blood from a blood source in situ, comprising: fractionating means having first and second independent passages therethrough for continuously producing a blood fraction, each of said passages having a blood inlet and a blood outlet and a blood flow channel providing communication therebetween, said fractionating means having a blood fraction collection channel and a blood fraction outlet communicating therewith, said fractionating means including wall means preventing fluid communication between said blood flow channels internally of said fractionating means, reservoir means, conduit means defining a closed path among the blood source and said fractionating means and said reservoir means, pump means for moving blood along said closed path, valve means coupled in said conduit means and operable between first and second conditions, said valve means in the first condition thereof permitting blood flow from the blood source and into said reservoir means while preventing blood flow from said reservoir means and to the blood source, said valve means in the second condition thereof permitting blood flow from said reservoir means and to the blood source while preventing blood flow from the blood source and to said reservoir means, control means coupled to said valve means for effecting operation thereof between the first and second conditions thereof, said pump means being operable when said valve means is in the first condition thereof for moving blood from the blood source through said first and second blood flow channels and to said reservoir means for continuously producing the blood fraction, said pump means being operable when said valve means is in the second condition thereof for moving blood from said reservoir means through said first and second blood flow channels and to the blood source for continuously producing the blood fraction, and means coupled to said blood fraction outlet for collecting the blood fraction produced.

19. The system of claim 18, wherein said control means includes means for repeatedly cycling said valve means between the first and second conditions thereof.

20. The system of claim 18, wherein said pump means includes a first pump disposed between the blood source and the inlet of said blood flow channel of said first passage, and a second pump disposed between the outlet of said blood flow channel of said first passage and the inlet of said blood flow channel of said second passage.

21. A system for continuously collecting plasma from a human donor thereof, comprising: processing means including means for ascertaining the initial volume of plasma in the donor based on donor specific data; fractionating means having first and second independent passages therethrough for continuously producing plasma, each of said passages having a blood inlet and a blood outlet and a blood flow channel providing communication therebetween, said fractionating means having a plasma collection channel and a plasma outlet communicating therewith, said fractionating means including wall means preventing fluid communication between said blood flow channels internally of said fractionating means; reservoir means; a single lumen needle adapted for insertion into a blood vessel of the donor; conduit means defining a closed path among said needle and said fractionating means and said reservoir means; pump means for moving blood along said closed path; valve means coupled in said conduit means and operable between first and second conditions, said valve means in the first condition thereof permitting blood flow from the donor and into said reservoir means while preventing blood flow from said reservoir means and to the donor, said valve means in the second condition thereof permitting blood flow from said reservoir means and to the donor while preventing blood flow from the donor and to said reservoir means; and control means coupled to said valve means for effecting operation thereof between the first and second conditions thereof; said pump means being operable when said valve means is in the first condition thereof for moving blood from the donor through the needle and through said first and second blood flow channels and to said reservoir means for continuously producing plasma, said pump means being operable when said valve means is in the second condition thereof for moving blood from said reservoir means through said first and second blood flow channels and through said needle to the donor for continuously producing plasma, and means coupled to said plasma outlet for collecting the plasma produced; said control means including means coupled to said valve means and to said collecting means for effecting repeated cycling between the first and second conditions thereof until a predetermined amount of plasma has been collected.

22. The system of claim 21, wherein the donor specific data is blood hematocrit and blood volume values.

23. The system of claim 21, and further comprising means for adding an anticoagulent to the blood in an amount equal to a predetermined percentage of the plasma concentration in the donor's blood.

* * * * *